(12) United States Patent
Sun

(10) Patent No.: US 12,310,985 B2
(45) Date of Patent: May 27, 2025

(54) COMPOSITION AND METHOD FOR TREATMENT OF DIABETES

(71) Applicant: SHENZHEN PROFOUND VIEW PHARMACEUTICAL TECHNOLOGY, Shenzhen (CN)

(72) Inventor: Taolei Sun, Wuhan (CN)

(73) Assignee: SHENZHEN PROFOUND VIEW PHARMACEUTICAL TECHNOLOGY, Shenzhen (CN)

( * ) Notice: Subject to any disclaimer, the term of this patent is extended or adjusted under 35 U.S.C. 154(b) by 749 days.

(21) Appl. No.: 17/753,307

(22) PCT Filed: Oct. 15, 2020

(86) PCT No.: PCT/CN2020/121079
§ 371 (c)(1),
(2) Date: Feb. 26, 2022

(87) PCT Pub. No.: WO2021/073563
PCT Pub. Date: Apr. 22, 2021

(65) Prior Publication Data
US 2022/0273706 A1    Sep. 1, 2022

(51) Int. Cl.
*A61K 33/242* (2019.01)
*A61K 47/54* (2017.01)
*A61K 47/64* (2017.01)
*A61P 3/10* (2006.01)

(52) U.S. Cl.
CPC .......... *A61K 33/242* (2019.01); *A61K 47/542* (2017.08); *A61K 47/64* (2017.08); *A61P 3/10* (2018.01)

(58) Field of Classification Search
CPC .......... A61K 33/242; A61K 47/64; A61P 3/10
See application file for complete search history.

(56) References Cited

U.S. PATENT DOCUMENTS

| 2011/0054202 A1 | 3/2011 | Snow |
| 2013/0216588 A1 | 8/2013 | Chou |
| 2019/0030069 A1 | 1/2019 | Sun |

FOREIGN PATENT DOCUMENTS

EP    3545948    10/2019

OTHER PUBLICATIONS

Negishi, Y et al. "Kinetic Stabilization of Growing Gold Clusters by Passivation with Thiolates" J. Phys. Chem. B, vol. 110, No. 25, 2006, pp. 12218-12221 (Year: 2006).*
Barathmanikanth et al. (2010) RAesneatrcih-oxidant effect of gold nanoparticles restrains hyperglycemic conditions in diabetic mice. Journal of Nanobiotechnology. 8:16.
Chen et al. (2018) Gold nanoparticles improve metabolic profile of mice fed a high-fat diet. Journal of Nanobiotechnology. 16:11.
Joshi et al. (2006) Gold Nanoparticles as Carriers for Efficient Transmucosal Insulin Delivery. Langmuir. 22: 300-305.
Qian et al. (2009) Size-Focusing Synthesis, Optical and Electrochemical Properties of Monodisperse Au38(SC2H4Ph)24 Nanoclusters. ACS Nano. 3: 3795-3803.
Zhang et al. (2012) Amyloid-b Induces Hepatic Insulin Resistance by .Activating JAK2/STAT3/SOCS-1 Signaling Pathway. Diabetes. 61: 1434.
Zhang et al. (2019) Gold nanoclusters for controlled insulin release and glucose regulation in diabetes. Nanoscale. 11: 6471.
Zuber et al. (2019) Biocompatible gold nanoclusters: synthetic strategies and biomedical prospects. Nanotechnology. 30: 352001.
W. Yan, L. Xu, C. Xu, W. Ma, H. Kuang, L. Wang and N. A. Kotov, Journal of the American Chemical Society 2012, 134, 15114.
X. Yuan, B. Zhang, Z. Luo, Q. Yao, D. T. Leong, N. Yan and J. Xie, Angewandte Chemie International Edition 2014, 53, 4623.

* cited by examiner

*Primary Examiner* — Andrew S Rosenthal
(74) *Attorney, Agent, or Firm* — Yihe Intellectual Property Service Company, Ltd; George Liu

(57) ABSTRACT

Disclosed are a pharmaceutical use of a gold cluster for the treatment of diabetes in a subject. The gold cluster comprises a gold core and a ligand modifying the gold core.

20 Claims, 21 Drawing Sheets

(a)

(b)

(c)

(d)

(a)
 (b)
 (c)
 (d)

(a)

(b)

(c)

(d)

(a)

(b)

(c)

(a)

(b)

(a)

(b)

(c)

(a)

(b)

(a)

(b)

(c)

(a)

(b)

(a)

(b)

(c)

(a)

(b)

(c)

(a)

(b)

COMPOSITION AND METHOD FOR TREATMENT OF DIABETES

FIELD OF THE INVENTION

The present invention relates to the technical field of diabetes, particularly to composition and methods for treatment of diabetes.

BACKGROUND OF THE INVENTION

Diabetes (also called mellitus (DM)) affects hundreds of millions of people worldwide, and is a group of metabolic disorders characterized by high blood sugar levels over a prolonged period. Symptoms of high blood sugar include increasedurination (polyuria), thirst (polydipsia), and hunger (polyphagia). If left untreated, diabetes causes acute and chronic complications. The acute complications include diabetic ketoacidosis, hyperosmolar hyperglycemic state, or death. The chronic complications include cardiovascular disease, stroke, chronic kidney disease, foot ulcers, and ocular damages.

Diabetes is due to either insulin deficiency (i.e. pancreas producing no or insufficient amount of insulin) or insulin resistance (i.e. cells inside the body not responding properly to insulin). Diabetes has been classified into three main types. Type 1 diabetes results from the pancreas' failure to produce enough insulin due to loss of beta cells. Type 1 diabetes is treated with insulin injections. Type 2 diabetes begins with insulin resistance, a condition in which cells fail to respond to insulin properly. Type 2 diabetes may be treated with medications with or without insulin. The progression of the disease may result in insulin deficiency. Gestational diabetes is the third main form, and occurs when pregnant women without a previous history of diabetes develop high blood sugar levels.

While available medications are helpful in lowering blood sugar levels, there is still an imperative need for new medications and methods for the treatment of diabetes.

SUMMARY OF THE INVENTION

The objective of the present invention is to provide a pharmaceutical composition and method for the treatment of diabetes.

In certain embodiments, the method for producing ligand-modified gold clusters (AuCs) comprises providing an $HAuCl_4$ solution; sequentially adding an acidic solution and a first ligand solution into the $HAuCl_4$ solution to form a first mixture solution; wherein the molar ratio between the first ligand and $HAuCl_4$ is in the range of 1:1 to 20:1; adding $NaBH_4$ solution into the first mixture solution to form a second mixture solution; wherein the molar ratio between $NaBH_4$ and $HAuCl_4$ is in the range of 1:1 to 10:1; adding an aprotic polar solvent to the second mixture solution to terminate reaction and to obtain a third mixture solution; centrifuging the third mixture solution to collect lower solid sediment; dissolving the collected lower solid sediment in a second ligand solution to obtain a fourth mixture solution and maintaining the fourth mixture solution for a period; wherein the molar ratio between the second ligand and $HAuCl_4$ is in the range of 1:1 to 20:1; centrifuging the fourth mixture solution to obtain supernatant; and dialyzing the supernatant in a dialysis bag with a predetermined cut-off molecular size.

In certain embodiments of the method, the $HAuCl_4$ solution is composed of a neutral or acidic solvent selected from the group consisting of water, methanol, ethanol, n-propanol, 1-propanol, 2-propanol, 1-butanol, 2-butanol, pentanol, pentane, formic acid, acetic acid, diethyl ether, acetone, anisole, ethyl formate, methyl acetate, ethyl acetate, propyl acetate, isopropyl acetate, butyl acetate, isobutyl acetate, tributyl methyl ether, dimethyl sulfoxide, 2-methyl-1-propanol, and a mixture of two or more thereof.

In certain embodiments of the method, the acidic solution is composed of an acid selected from the group consisting of hydrochloric acid, phosphoric acid, sulfuric acid, acetic acid, propionic acid, butyric acid, and a mixture of two or more thereof.

In certain embodiments of the method, the first ligand and second ligand are selected from L-cysteine, D-cysteine and other cysteine derivatives; cysteine-containing oligopeptides and their derivatives; other thiol-containing compounds; and a mixture of two or more thereof.

In certain embodiments of the method, the first ligand solution and second ligand solution are composed of a solvent selected from the group consisting of water, methanol, ethanol, n-propanol, 1-propanol, 2-propanol, 1-butanol, 2-butanol, pentanol, ethyl formate, methyl acetate, ethyl acetate, propyl acetate, isopropyl acetate, butyl acetate, isobutyl acetate, 2-methyl-1-propanol, and a mixture of two or more thereof.

In certain embodiments of the method, the $NaBH_4$ solution is composed of a solvent selected from the group consisting of water, methanol, ethanol, n-propanol, 1-propanol, 2-propanol, 1-butanol, 2-butanol, pentanol, ethyl formate, methyl acetate, ethyl acetate, propyl acetate, isopropyl acetate, butyl acetate, isobutyl acetate, 2-methyl-1-propanol, and a mixture of two or more thereof.

In certain embodiments of the method, the aprotic polar solvent is selected from the group consisting of dimethyl sulfoxide (DMSO), acetone, acetonitrile, dimethylformamide (DMF), dimethylacetamide (DMAC), hexamethylphosphoramide (HMP), chloroform, carbon tetrachloride, pyridine, and a mixture of two or more thereof.

In certain embodiments of the method, the period for maintaining the fourth mixture solution is in the range of 3-24 hours.

In certain embodiments, the method further comprises lyophilizing the dialyzed supernatant to obtain an AuCs powder.

In certain embodiments, the present invention provides an AuCs powder produced by the method of the present invention.

Certain embodiments of the present invention use a gold cluster (AuC) for manufacture of a medicament for the treatment of diabetes in a subject, wherein said AuC comprises a gold core; and a ligand modifying the gold core.

In certain embodiments of the use, the gold core has a diameter smaller than 3 nm. In certain embodiments, the gold core has a diameter in the range of 0.5-2.6 nm.

In certain embodiments of the use, the ligand is one selected from the group consisting of L-cysteine and its derivatives, D-cysteine and its derivatives, cysteine-containing oligopeptides and their derivatives, and other thiol-containing compounds.

In certain embodiments of the use, the L-cysteine and its derivatives are selected from the group consisting of L-cysteine, N-isobutyryl-L-cysteine (L-NIBC), and N-acetyl-L-cysteine (L-NAC), and the D-cysteine and its derivatives are selected from the group consisting of D-cysteine, N-isobutyryl-D-cysteine (D-NIBC), and N-acetyl-D-cysteine (D-NAC).

In certain embodiments of the use, the cysteine-containing oligopeptides and their derivatives are cysteine-containing dipeptides, cysteine-containing tripeptides or cysteine-containing tetrapeptides.

In certain embodiments of the use, the cysteine-containing dipeptides are selected from the group consisting of L-cysteine-L-arginine dipeptide (CR), L-arginine-L-cysteine dipeptide (RC), L-histidine-L-cysteine dipeptide (HC), and L-cysteine-L-histidine dipeptide (CH).

In certain embodiments of the use, the cysteine-containing tripeptides are selected from the group consisting of glycine-L-cysteine-L-arginine tripeptide (GCR), L-proline-L-cysteine-L-arginine tripeptide (PCR), L-lysine-L-cysteine-L-proline tripeptide (KCP), and L-glutathione (GSH).

In certain embodiments of the use, the cysteine-containing tetrapeptides are selected from the group consisting of glycine-L-serine-L-cysteine-L-arginine tetrapeptide (GSCR), and glycine-L-cysteine-L-serine-L-arginine tetrapeptide (GCSR).

In certain embodiments of the use, the other thiol-containing compounds are selected from the group consisting of 1-[(2S)-2-methyl-3-thiol-1-oxopropyl]-L-proline, thioglycollic acid, mercaptoethanol, thiophenol, D-3-trolovol, N-(2-mercaptopropionyl)-glycine, and dodecyl mercaptan.

The objectives and advantages of the invention will become apparent from the following detailed description of preferred embodiments thereof in connection with the accompanying drawings.

DESCRIPTION OF THE DRAWINGS

Preferred embodiments according to the present invention will now be described with reference to the Figures, in which like reference numerals denote like elements.

DETAILED DESCRIPTION OF THE EMBODIMENTS

Figure 1:
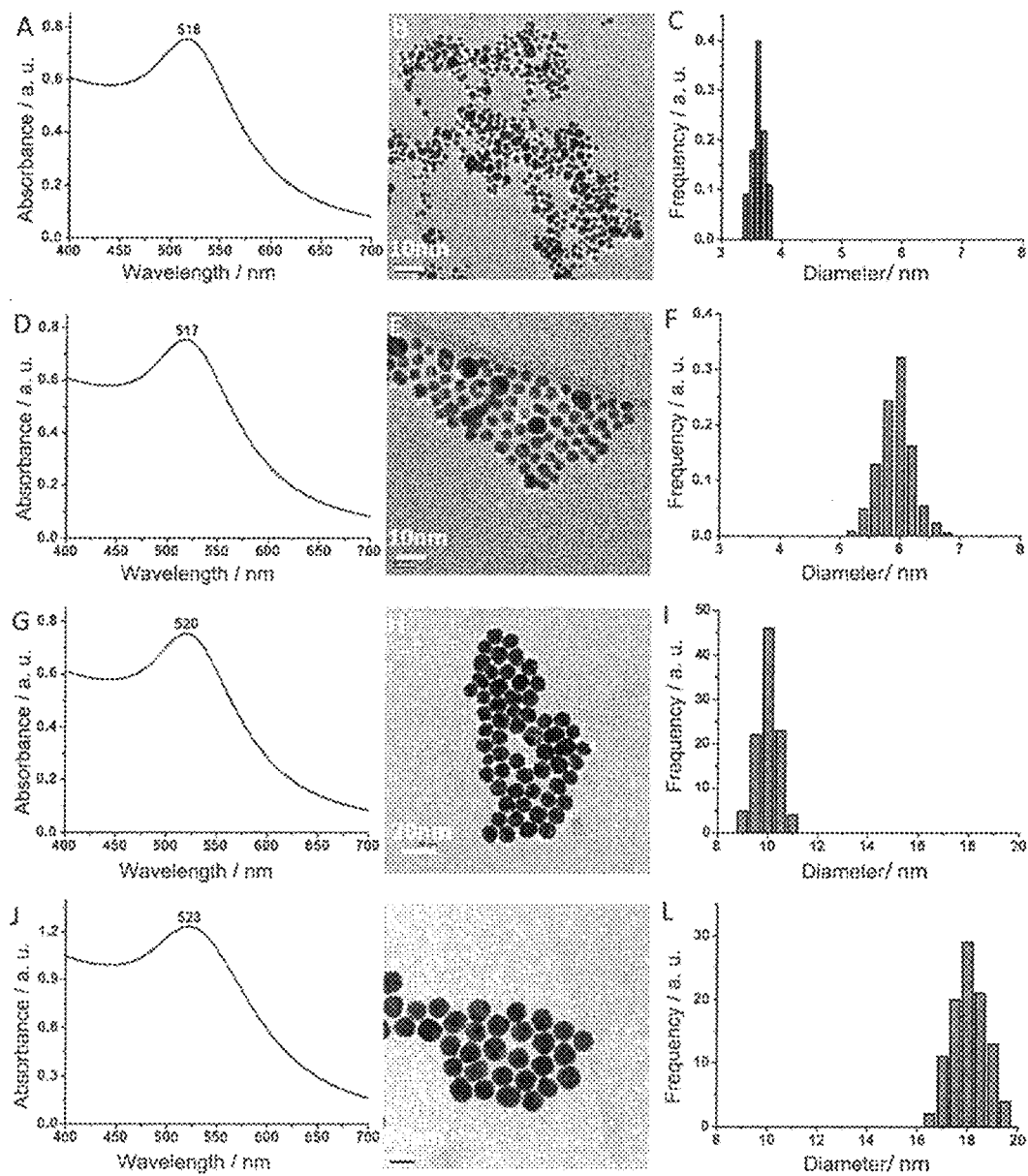
FIG. 1 shows ultraviolet-visible (UV) spectrums, transmission electron microscope (TEM) images and particle size distribution diagrams of ligand L-NIBC-modified gold nanoparticles (L-NIBC-AuNPs) with different particle sizes.

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

Gold clusters (AuCs) are a special form of gold existing between gold atoms and gold nanoparticles. AuCs have a size smaller than 3 nm, and are composed of only several to a few hundreds of gold atoms, leading to the collapse of face-centered cubic stacking structure of gold nanoparticles. As a result, AuCs exhibit molecule-like discrete electronic structures with distinct HOMO-LUMO gap unlike the continuous or quasi-continuous energy levels of gold nanoparticles. This leads to the disappearance of surface plasmon resonance effect and the corresponding plasmon resonance absorption band (520±20 nm) at uv-vis spectrum that possessed by conventional gold nanoparticles.

The present invention provides a ligand-modified AuC.

In certain embodiments, the ligand-modified AuC comprises a ligand and a gold core with a diameter in the range of 0.5-3 nm. In certain embodiments, the diameter of the gold core is in the range of 0.5-2.6 nm.

In certain embodiments, the ligand of the ligand-modified AuC is a thiol-containing compound or oligopeptide. The ligand modifies the gold core to form a ligand-modified AuC via Au—S bond.

In certain embodiments, the ligand is, but not limited to, L-cysteine, D-cysteine, or a cysteine derivative. In certain embodiments, the cysteine derivative is N-isobutyryl-L-cysteine (L-NIBC), N-isobutyryl-D-cysteine (D-NIBC), N-acetyl-L-cysteine (L-NAC), or N-acetyl-D-cysteine (D-NAC).

In certain embodiments, the ligand is, but not limited to, a cysteine-containing oligopeptide and its derivatives. In certain embodiments, the cysteine-containing oligopeptide is a cysteine-containing dipeptide. In certain embodiments, the cysteine-containing dipeptide is L-cysteine-L-arginine dipeptide (CR), L-arginine-L-cysteine dipeptide (RC), or L-cysteine-L-histidine dipeptide (CH). In certain embodiments, the cysteine-containing oligopeptide is a cysteine-containing tripeptide. In certain embodiments, the cysteine-containing tripeptide is glycine-L-cysteine-L-arginine tripeptide (GCR), L-proline-L-cysteine-L-arginine tripeptide (PCR), or L-glutathione (GSH). In certain embodiments, the cysteine-containing oligopeptide is a cysteine-containing tetrapeptide. In certain embodiments, the cysteine-containing tetrapeptide is glycine-L-serine-L-cysteine-L-arginine tetrapeptide (GSCR) or glycine-L-cysteine-L-serine-L-arginine tetrapeptide (GCSR).

In certain embodiments, the ligand is a thiol-containing compound. In certain embodiments, thiol-containing compound is 1-[(2S)-2-methyl-3-thiol-1-oxopropyl]-L-proline, thioglycollic acid, mercaptoethanol, thiophenol, D-3-trolovol, or dodecyl mercaptan.

The present invention provides a pharmaceutical composition for the treatment of diabetes in a subject. In certain embodiments, the subject is human. In certain embodiments, the subject is a pet animal such as a dog.

In certain embodiments, the pharmaceutical composition comprises a ligand-modified AuC as disclosed above and a pharmaceutically acceptable excipient. In certain embodiments, the excipient is phosphate-buffered solution, or physiological saline.

The present invention provides a use of the above disclosed AuCs for manufacturing a medication for the treatment of diabetes in a subject.

The present invention provides a use of the above disclosed AuCs for treating diabetes in a subject or a method for treating diabetes in subject using the above disclosed AuCs. In certain embodiments, the method for treatment comprises administering a pharmaceutically effective amount of AuCs to the subject. The pharmaceutically effective amount can be ascertained by routine in vivo studies.

Figure 12:
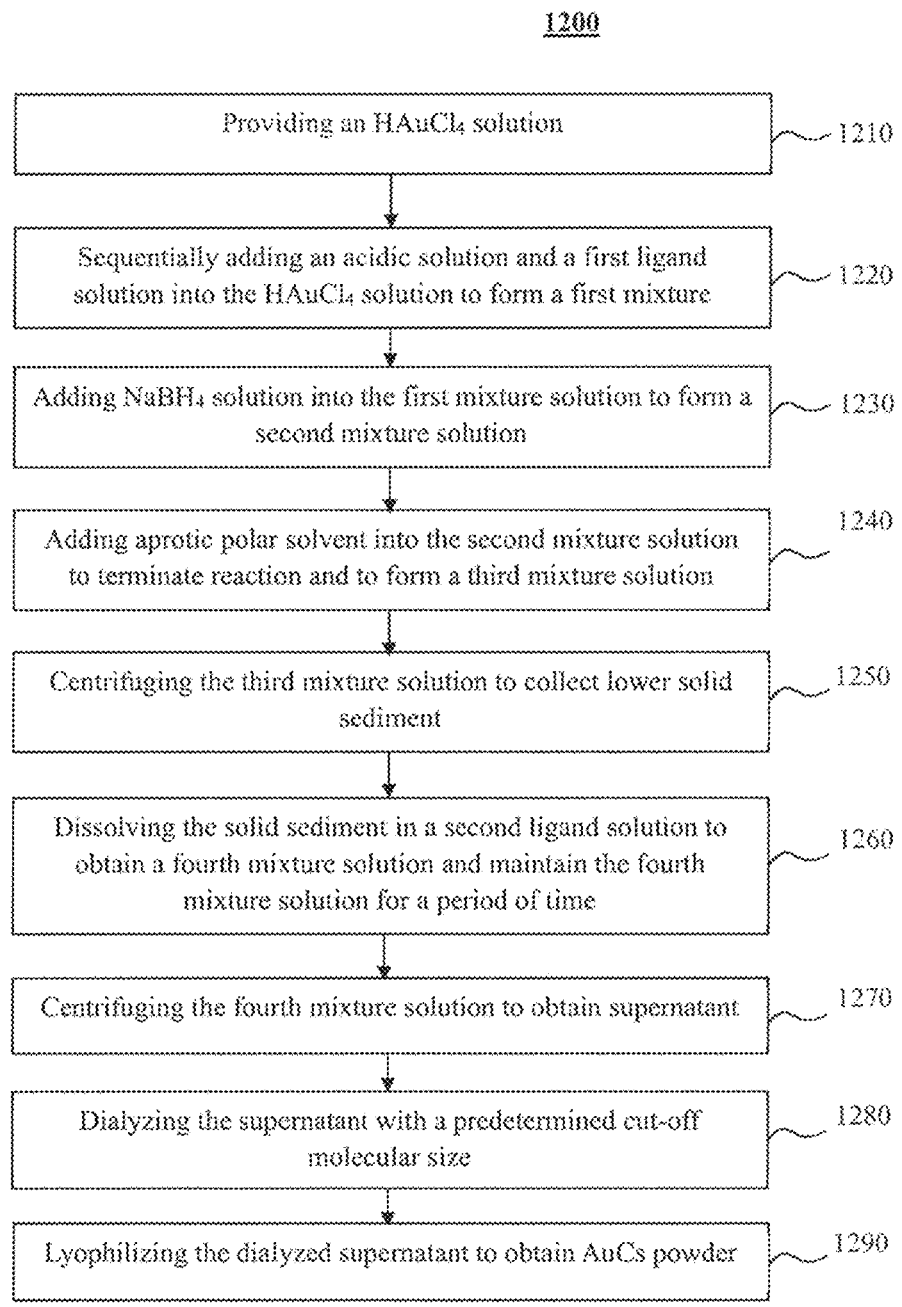
FIG. 12 shows a flowchart of the method for producing AuCs in accordance with certain embodiments of the present invention.

The present invention provides a method for producing ligand-modified gold clusters (AuCs). Referring now to FIG. 12, there is provided a flowchart of the method in accordance with certain embodiments of the present invention. The method 1200 comprises:

providing an HAuCl$_4$ solution 1210, wherein the HAuCl$_4$ solution is composed of a neutral or acidic solvent selected from the group consisting of water, methanol, ethanol, n-propanol, 1-propanol, 2-propanol, 1-butanol, 2-butanol, pentanol, pentane, formic acid, acetic acid, diethyl ether, acetone, anisole, ethyl formate, methyl acetate, ethyl acetate, propyl acetate, isopropyl acetate, butyl acetate, isobutyl acetate, tributyl methyl ether, dimethyl sulfoxide, 2-methyl-1-propanol, and a mixture of two or more thereof. In certain embodiments, the solvent is methanol. In certain embodiments, the HAuCl$_4$ solution is pre-cooled to 0° C. or lower without light with slow stirring. In certain embodiments, the concentration of HAuCl$_4$ in the HAuCl$_4$ solution is the range of 1-20 g/L, preferably 2-10 g/L. In certain embodiments, when the total volume of the complete reaction is designated as 1 volume, the HAuCl$_4$ solution is in the range of 0.1-0.7 volume, preferably in the range of 0.2-0.5 volume.

sequentially adding an acidic solution and a first ligand solution into the HAuCl$_4$ solution to form a first mixture solution 1220. In certain embodiments, the acidic solution is composed of an acid selected from the group consisting of hydrochloric acid, phosphoric acid, sulfuric acid, acetic acid, propionic acid, butyric acid, and a mixture of two or more thereof. In certain embodiments, the acidic solution is in the range of 0.01-0.1 volume. In certain embodiments, the acidic solution ensures that the reaction is performed at pH<5, preferably at a pH in the range of 1-3, most preferably at a pH in the range of 1-2. In certain embodiments, the reaction temperature is lower than 4° C. In certain embodiments, the first ligand is selected from L-cysteine, D-cysteine and other cysteine derivatives such as N-isobutyryl-L-cysteine (L-NIBC), N-isobutyryl-D-cysteine (D-NIBC), N-acetyl-L-cysteine (L-NAC), and N-acetyl-D-cysteine (D-NAC), cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol, dodecyl mercaptan, and a mixture of two or more thereof. In certain embodiments, the first ligand solution is composed of a solvent selected from the group consisting of water, methanol, ethanol, n-propanol, 1-propanol, 2-propanol, 1-butanol, 2-butanol, pentanol, ethyl formate, methyl acetate, ethyl acetate, propyl acetate, isopropyl acetate, butyl acetate, isobutyl acetate, 2-methyl-1-propanol, and a mixture of two or more thereof. In certain embodiments, the first ligand concentration in the first ligand solution is in the range of 5-150 g/L, preferably 20-80 g/L. In certain embodiments, the first ligand solution is in the range of 0.01-0.6 volume. In certain embodiments, the molar ratio between the first ligand and $HAuCl_4$ is in the range of 1:1 to 20:1, preferably 2:1 to 5:1. In certain embodiments, the reaction time of the first mixture solution is in a period of 0.5-2 hours.

adding $NaBH_4$ solution into the first mixture solution to form a second mixture solution 1230. In certain embodiments, the $NaBH_4$ solution is composed of a solvent selected from the group consisting of water, methanol, ethanol, n-propanol, 1-propanol, 2-propanol, 1-butanol, 2-butanol, pentanol, ethyl formate, methyl acetate, ethyl acetate, propyl acetate, isopropyl acetate, butyl acetate, isobutyl acetate, 2-methyl-1-propanol, and a mixture of two or more thereof. In certain embodiments, the $NaBH_4$ concentration of the $NaBH_4$ solution is in the range of 1-100 g/L, preferably 10-50 g/L. In certain embodiments, the $NaBH_4$ solution is in the range of 0.01-0.6 volume. In certain embodiments, the molar ratio between $NaBH_4$ and $HAuCl_4$ is in the range of 1:1 to 10:1, preferably 1:1 to 5:1. In certain embodiments, the reaction period of the second mixture solution is in the range of 5-100 minutes.

adding an aprotic polar solvent to the second mixture solution to terminate reaction and to obtain a third mixture solution 1240. In certain embodiments, the aprotic polar solvent is selected from the group consisting of dimethyl sulfoxide (DMSO), acetone, acetonitrile, dimethylformamide (DMF), dimethylacetamide (DMAC), hexamethylphosphoramide (HMP), chloroform, carbon tetrachloride, pyridine, and a mixture of two or more thereof.

centrifuging the third mixture solution to collect solid sediment 1250. In certain embodiments, the centrifugation is in the range of 1,500-6,000 g, preferably 2,000-5,000 g.

dissolving the solid sediment from step 1250 in a second ligand solution to obtain a fourth mixture solution and maintain the fourth mixture solution for a period of time 1260. In certain embodiments, the second ligand is selected from L-cysteine, D-cysteine and other cysteine derivatives such as N-isobutyryl-L-cysteine (L-NIBC), N-isobutyryl-D-cysteine (D-NIBC), N-acetyl-L-cysteine (L-NAC), and N-acetyl-D-cysteine (D-NAC), cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol, dodecyl mercaptan, and a mixture of two or more thereof. In certain embodiments, the second ligand solution is composed of a solvent selected from the group consisting of water, methanol, ethanol, n-propanol, 1-propanol, 2-propanol, 1-butanol, 2-butanol, pentanol, ethyl formate, methyl acetate, ethyl acetate, propyl acetate, isopropyl acetate, butyl acetate, isobutyl acetate, 2-methyl-1-propanol, and a mixture of two or more thereof. In certain embodiments, the first ligand and second ligand are the same. In certain embodiments, the solvents in the first ligand solution and second ligand solution are the same. In certain embodiments, the second ligand concentration in the second ligand solution is in the range of 5-100 g/L, preferably 20-50 g/L. In certain embodiments, the second ligand solution is in the range of 0.1-10 volume, preferably 1-2 volume. It is to be noted that the 'volume' here refers to the same designation as stated above. In certain embodiments, the molar ratio between the second ligand and $HAuCl_4$ is in the range of 1:1 to 20:1, preferably 2:1 to 5:1. In certain embodiments, the period of time is in the range of 3-24 hours.

centrifuging the fourth mixture solution to obtain the supernatant 1270. In certain embodiments, the centrifugation is in the range of 2,000-8,000 g, preferably 3,000-5,000 g. In certain embodiments, the time of centrifugation is in the range of 3-50 minutes, preferably 5-15 minutes.

dialyzing the supernatant in a dialysis bag with a predetermined cut-off molecular size 1280. In certain embodiments, the cut-off molecular size is in the range of 500-5,000 Dolton. In certain embodiments, the dialysis is in ultrapure water, and the water is changed for 3-10 times.

lyophilizing the dialyzed supernatant to obtain an AuCs powder 1290.

The following examples are provided for the sole purpose of illustrating the principles of the present invention; they are by no means intended to limit the scope of the present invention.

EXAMPLES

Embodiment 1. Preparation of Ligand-Modified AuCs 1.1 Dissolving $HAuCl_4$ in methanol, water, ethanol, n-propanol, or ethyl acetate to get a solution A in which the concentration of $HAuCl_4$ is 0.01~0.03M;

1.2 Dissolving a ligand in a solvent to get a solution B in which the concentration of the ligand is 0.01~0.18M; the ligand includes, but not limited to, L-cysteine, D-cysteine and other cysteine derivatives such as N-isobutyryl-L-cysteine (L-NIBC), N-isobutyryl-D-cysteine (D-NIBC), N-acetyl-L-cysteine (L-NAC), and N-acetyl-D-cysteine (D-NAC), cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol and dodecyl mercaptan; the solvent is one or more of methanol, ethyl acetate, water, ethanol, n-propanol, pentane, formic acid, acetic acid, diethyl ether, acetone, anisole, 1-propanol, 2-propanol, 1-butanol, 2-butanol, pentanol, butyl acetate, tributyl methyl ether, isopropyl acetate, dimethyl sulfoxide, ethyl formate, isobutyl acetate, methyl acetate, 2-methyl-1-propanol and propyl acetate;

1.3 Mixing solution A and solution B so that the mole ratio between $HAuCl_4$ and ligand is 1: (0.01~100), stirring them in an ice bath for 0.1~48 h, adding 0.025~0.8M $NaBH_4$ water, ethanol or methanol solution, continuing to stir in an ice water bath and react for 0.1~12 h. The mole ratio between $NaBH_4$ and ligand is 1: (0.01~100);

1.4 Using MWCO 3K~30K ultrafiltration tubes to centrifuge the reaction solution at 8000~17500 r/min by gradient for 10~100 min after the reaction ends to obtain ligand-modified AuCs precipitate in different average particle sizes. The aperture of the filtration membranes for ultrafiltration tubes of different MWCOs directly decides the size of ligand-modified AuCs that can pass the membranes. This step may be optionally omitted;

1.5 Dissolving the ligand-modified AuCs precipitate in different average particle sizes obtained in step (1.4) in water, putting it in a dialysis bag and dialyzing it in water at room temperature for 1~7 days;

1.6 Freeze-drying ligand-modified AuCs for 12~24 h after dialysis to obtain a powdery or flocculant substance, i.e., ligand-modified AuCs.

As detected, the particle size of the powdery or flocculant substance obtained by the foregoing method is smaller than 3 nm (distributed in 0.5~2.6 nm in general). No obvious absorption peak at 520 nm. It is determined that the obtained powder or floc is ligand-modified AuCs.

Embodiment 2. Preparation and Characterization of AuCs Modified With Different Ligands 2.1 Preparation of L-NIBC-AuCs Taking ligand L-NIBC for example, the preparation and confirmation of AuCs modified with ligand L-NIBC are detailed.

2.1.1 Weigh 1.00 g of $HAuCl_4$ and dissolve it in 100 mL of methanol to obtain a 0.03M solution A;

2.1.2 Weigh 0.57 g of L-NIBC and dissolve it in 100 mL of glacial acetic acid (acetic acid) to obtain a 0.03M solution B;

2.1.3 Measure 1 mL of solution A, mix it with 0.5 mL, 1 mL, 2 mL, 3 mL, 4 mL, or 5 mL of solution B respectively (i.e. the mole ratio between $HAuCl_4$ and L-NIBC is 1:0.5, 1:1, 1:2, 1:3, 1:4, 1:5 respectively), react in an ice bath under stirring for 2 h, quickly add 1 mL of freshly prepared 0.03M (prepared by weighing 11.3 mg of $NaBH_4$ and dissolving it in 10 mL of ethanol) $NaBH_4$ ethanol solution when the solution turns colorless from bright yellow, continue the reaction for 30 min after the solution turns dark brown, and add 10 mL of acetone to terminate the reaction.

2.1.4 After the reaction, the reaction solution is subjected to gradient centrifugation to obtain L-NIBC-AuCs powder with different particle sizes. Specific method: After the reaction is completed, the reaction solution is transferred to an ultrafiltration tube with MWCO of 30K and a volume of 50 mL, and centrifuged at 10000 r/min for 20 min, and the retentate in the inner tube is dissolved in ultrapure water to obtain powder with a particle size of about 2.6 nm. Then, the mixed solution in the outer tube is transferred to an ultrafiltration tube with a volume of 50 mL and MWCO of 10K, and centrifuged at 13,000 r/min for 30 min. The retentate in the inner tube is dissolved in ultrapure water to obtain powder with a particle size of about 1.8 nm. Then the mixed solution in the outer tube is transferred to an ultrafiltration tube with a volume of 50 mL and MWCO of 3K, and centrifuged at 17,500 r/min for 40 min. The retentate in the inner tube is dissolved in ultrapure water to obtain powder with a particle size of about 1.1 nm.

2.1.5 Precipitate the powder in three different particle sizes obtained by gradient centrifugation, remove the solvent respectively, blow the crude product dry with $N_2$, dissolve it in 5 mL of ultrapure water, put it in a dialysis bag (MWCO is 3 KDa), put the dialysis bag in 2 L of ultrapure water, change water every other day, dialyze it for 7 days, freeze-dry it and keep it for future use.

2.2 Characterization of L-NIBC-AuCs

Characterization experiment was conducted for the powder obtained above (L-NIBC-AuCs). Meanwhile, ligand L-NIBC-modified gold nanoparticles (L-NIBC-AuNPs) are used as control. The method for preparing gold nanoparticles with ligand being L-NIBC refers to the reference (W. Yan, L. Xu, C. Xu, W. Ma, H. Kuang, L. Wang and N. A. Kotov, Journal of the American Chemical Society 2012, 134, 15114; X. Yuan, B. Zhang, Z. Luo, Q. Yao, D. T. Leong, N. Yan and J. Xie, Angewandte Chemie International Edition 2014, 53, 4623).

2.2.1 Observation of the morphology by transmission electron microscope (TEM)

The test powders (L-NIBC-AuCs sample and L-NIBC-AuNPs sample) were dissolved in ultrapure water to 2 mg/L as samples, and then test samples were prepared by hanging drop method. More specifically, 5 µL of the samples were dripped on an ultrathin carbon film, volatized naturally till the water drop disappeared, and then observe the morphology of the samples by JEM-2100F STEM/EDS field emission high-resolution TEM.

Figure 2:
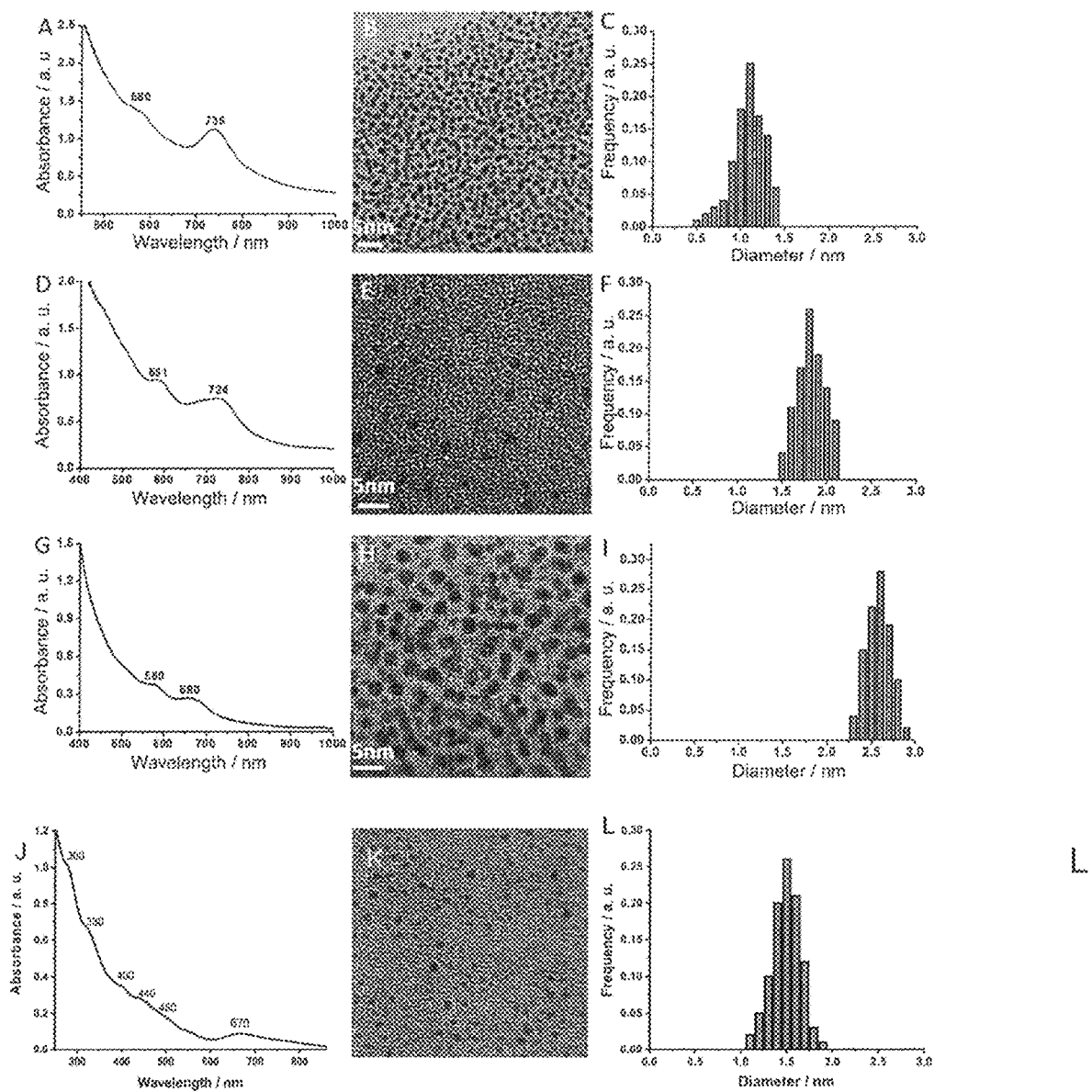
FIG. 2 shows ultraviolet-visible (UV) spectrums, TEM images and particle size distribution diagrams of ligand L-NIBC-modified gold clusters (L-NIBC-AuCs) with different particle sizes.

The four TEM images of L-NIBC-AuNPs are shown in panels B, E, H, and K of FIG. 1; the three TEM images of L-NIBC-AuCs are shown in panels B, E, and H of FIG. 2.

The images in FIG. 2 indicate that each of L-NIBC-AuCs samples has a uniform particle size and good dispersibility, and the average diameter of L-NIBC-AuCs (refer to the diameter of gold core) is 1.1 nm, 1.8 nm and 2.6 nm respectively, in good accordance with the results in panels C, F and I of FIG. 2. In comparison, L-NIBC-AuNPs samples have a larger particle size. Their average diameter (refer to the diameter of gold core) is 3.6 nm, 6.0 nm, 10.1 nm and 18.2 nm respectively, in good accordance with the results in panels C, F, I and L of FIG. 1.

2.2.2 Ultraviolet (UV)-visible (vis) absorption spectra

The test powders (L-NIBC-AuCs sample and L-NIBC-AuNPs sample) were dissolved in ultrapure water till the concentration was 10 mg·$L^{-1}$, and the UV-vis absorption spectra were measured at room temperature. The scanning range was 190-1100 nm, the sample cell was a standard quartz cuvette with an optical path of 1 cm, and the reference cell was filled with ultrapure water.

The UV-vis absorption spectra of the four L-NIBC-AuNPs samples with different sizes are shown in panels A, D, G and J of FIG. 1, and the statistical distribution of particle size is shown in panels C, F, I and L of FIG. 1; the UV-vis absorption spectra of three L-NIBC-AuCs samples with different sizes are shown in panels A, D and G of FIG. 2, and the statistical distribution of particle size is shown in panels C, F and I of FIG. 2.

FIG. 1 indicates that due to the surface plasmon effect, L-NIBC-AuNPs had an absorption peak at about 520 nm.

The position of the absorption peak is relevant with particle size. When the particle size is 3.6 nm, the UV absorption peak appears at 516 nm; when the particle size is 6.0 nm, the UV absorption peak appears at 517 nm; when the particle size is 10.1 nm, the UV absorption peak appears at 520 nm, and when the particle size is 18.2 nm, the absorption peak appears at 523 nm. None of the four samples has any absorption peak above 560 nm.

FIG. 2 indicates that in the UV absorption spectra of three L-NIBC-AuCs samples with different particle sizes, the surface plasmon effect absorption peak at 520 nm disappeared, and two obvious absorption peaks appeared above 560 nm and the positions of the absorption peaks varied slightly with the particle sizes of AuCs. This is because AuCs exhibit molecule-like properties due to the collapse of the face-centered cubic structure, which leads to the discontinuity of the density of states of AuCs, the energy level splitting, the disappearance of plasmon resonance effect and the appearance of a new absorption peak in the long-wave direction. It could be concluded that the three powder samples in different particle sizes obtained above are all ligand-modified AuCs.

2.2.3 Fourier transform infrared spectroscopy

Infrared spectra were measured on a VERTEX8OV Fourier transform infrared spectrometer manufactured by Bruker in a solid powder high vacuum total reflection mode. The scanning range is 4000-400 $cm^{-1}$ and the number of scans is 64. Taking L-NIBC-AuCs samples for example, the test samples were L-NIBC-AuCs dry powder with three different particle sizes and the control sample was pure L-NIBC powder. The results are shown in FIG. 3.

Figure 3:
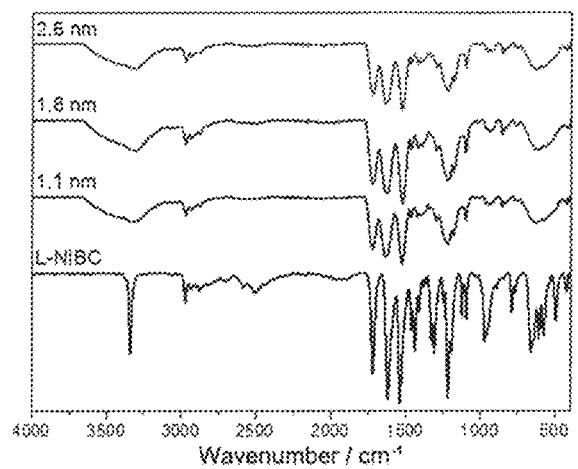
FIG. 3 shows infrared spectra of L-NIBC-AuCs with different particle sizes.

FIG. 3 shows the infrared spectrum of L-NIBC-AuCs with different particle sizes. Compared with pure L-NIBC (the curve at the bottom), the S—H stretching vibrations of L-NIBC-AuCs with different particle sizes all disappeared completely at 2500-2600 $cm^{-1}$, while other characteristic peaks of L-NIBC were still observed, proving that L-NIBC molecules were successfully anchored to the surface of AuCs via Au—S bond. The Figure also shows that the infrared spectrum of the ligand-modified AuCs is irrelevant with its size.

AuCs modified by other ligands were prepared by a method similar to the above method, except that the solvent of solution B, the feed ratio between $HAuCl_4$ and ligand, the reaction time and the amount of $NaBH_4$ added were slightly adjusted. For example: when L-cysteine, D-cysteine, N-isobutyryl-L-cysteine (L-NIBC) or N-isobutyryl-D-cysteine (D-NIBC) is used as the ligand, acetic acid is selected as the solvent; when dipeptide CR, dipeptide RC or 1-[(2S)-2-methyl-3-thiol-1-oxopropyl]-L-proline is used as the ligand, water is selected as the solvent, and so on and so forth; other steps are similar, so no further details are provided herein.

The present invention prepared and obtained a series of ligand-modified AuCs by the foregoing method. The ligands and the parameters of the preparation process are shown in Table 1.

TABLE 1

Preparation parameters of AuCs modified with different ligands in the present invention

|  | Ligand | Solvent used for solution B | Feed ratio between $HAuCl_4$ and ligand | Time of reaction in an ice bath under stirring before addition of $NaBH_4$ | Mole ratio between $HAuCl_4$ and $NaBH_4$ | Time of reaction in an ice bath under stirring after addition of $NaBH_4$ |
|---|---|---|---|---|---|---|
| 1 | L-cysteine | Acetic acid | 1:3 | 2 h | 1:2 | 0.5 h |
| 2 | D-cysteine | Acetic acid | 1:3 | 2 h | 1:2 | 0.5 h |
| 3 | N-acetyl-L-cysteine | Ethanol | 1:4 | 1 h | 1:1 | 0.5 h |
| 4 | N-acetyl-D-cysteine | Ethanol | 1:4 | 1 h | 1:1 | 0.5 h |
| 5 | L-NIBC | Water | 1:4 | 0.5 h | 1:2 | 0.5 h |
| 6 | D-NIBC | Water | 1:4 | 0.5 h | 1:2 | 0.5 h |
| 7 | Other cysteine derivatives | Soluble solvent | 1:(0.1~100) | 0.5 h~24 h | 1:(0.1~100) | 0.1~24 h |
| 8 | CR | Water | 1:4 | 22 h | 2:1 | 0.5 h |
| 9 | RC | Water | 1:4 | 20 h | 2:1 | 0.5 h |
| 10 | HC | Water | 1:3 | 12 h | 1:2 | 2 h |
| 11 | CH | Ethanol | 1:4 | 16 h | 1:3 | 3 h |
| 12 | GSH | Water | 1:2 | 12 h | 1:1 | 3 h |
| 13 | KCP | Water | 1:3 | 15 h | 1:2 | 1 h |
| 14 | PCR | Water | 1:4 | 16 h | 1:3 | 2 h |
| 15 | GSCR | Water | 1:4 | 16 h | 1:3 | 1.5 h |
| 16 | GCSR | Water | 1:3 | 12 h | 1:2 | 2 h |
| 17 | Other oligopeptides containing cysteine | Soluble solvent | 1:(0.1~100) | 0.5 h~24 h | 1:(0.1~100) | 0.1~24 h |
| 18 | 1-[(2S)-2-methyl-3-thiol-1-oxopropyl]-L-proline | Water | 1:8 | 2 h | 1:7 | 1 h |
| 19 | Mercaptoethanol | Ethanol | 1:2 | 2 h | 1:1 | 1 h |
| 20 | Thioglycollic acid | Acetic acid | 1:2 | 2 h | 1:1 | 1 h |
| 21 | Thiophenol | Ethanol | 1:5 | 5 h | 1:1 | 1 h |
| 22 | D-3-trolovol | Water | 1:2 | 2 h | 1:1 | 1 h |
| 23 | N-(2-mercaptopropionyl)-glycine | Water | 1:2 | 2 h | 1:1 | 1 h |
| 24 | Dodecyl mercaptan | Methanol | 1:5 | 5 h | 1:1 | 1 h |
| 25 | Other compounds containing thiol | Soluble solvent | 1:(0.01~100) | 0.5 h~24 h | 1:(0.1~100) | 0.1~24 h |

Figure 4:
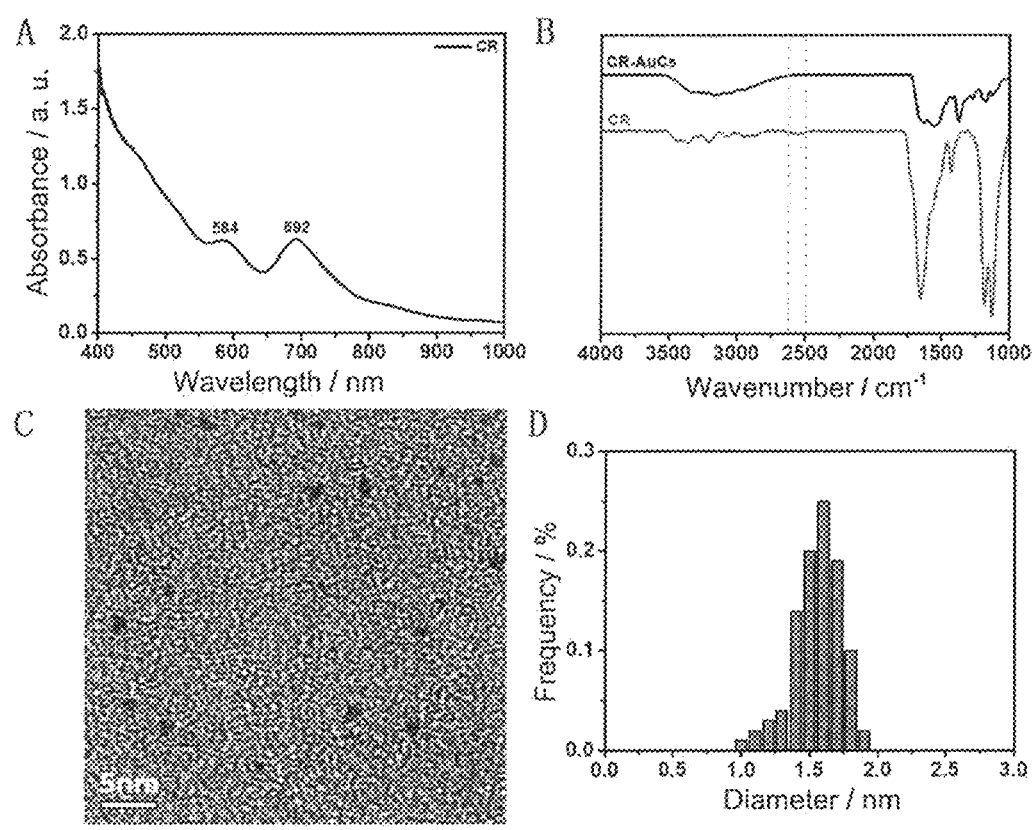
FIG. 4 shows UV, infrared, TEM, and particle size distribution diagrams of ligand CR-modified gold clusters (CR-AuCs).
Figure 5:
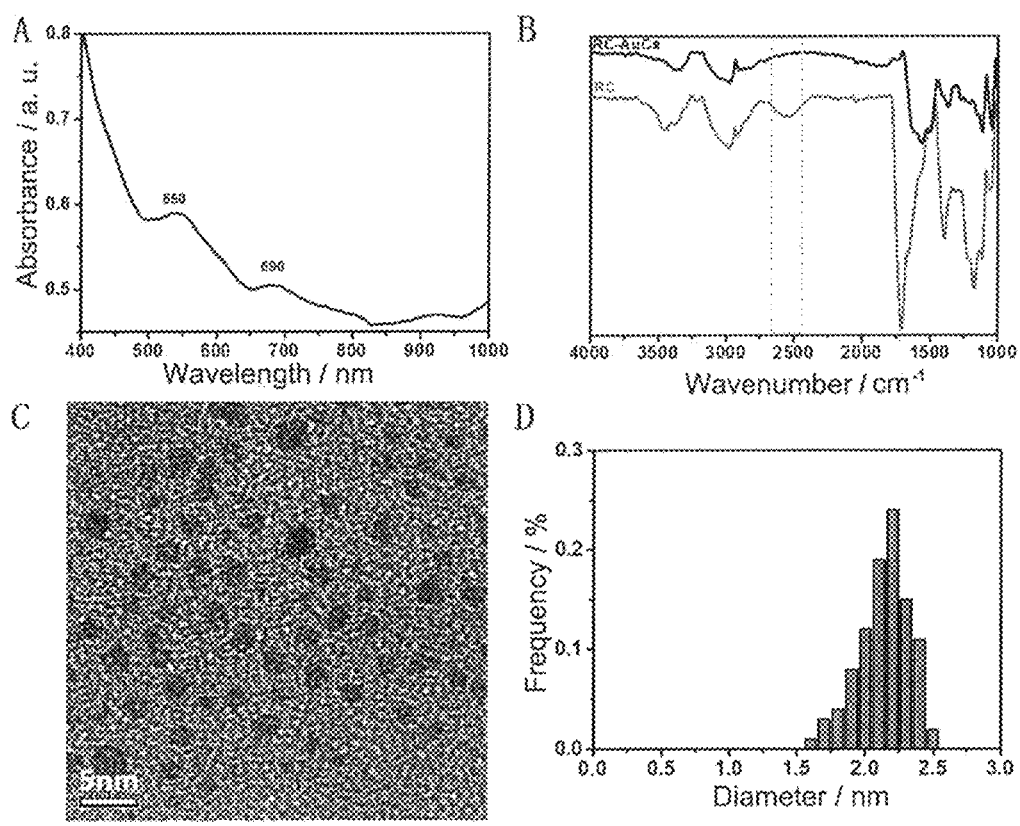
FIG. 5 shows UV, infrared, TEM, and particle size distribution diagrams of ligand RC-modified gold clusters (RC-AuCs).
Figure 6:
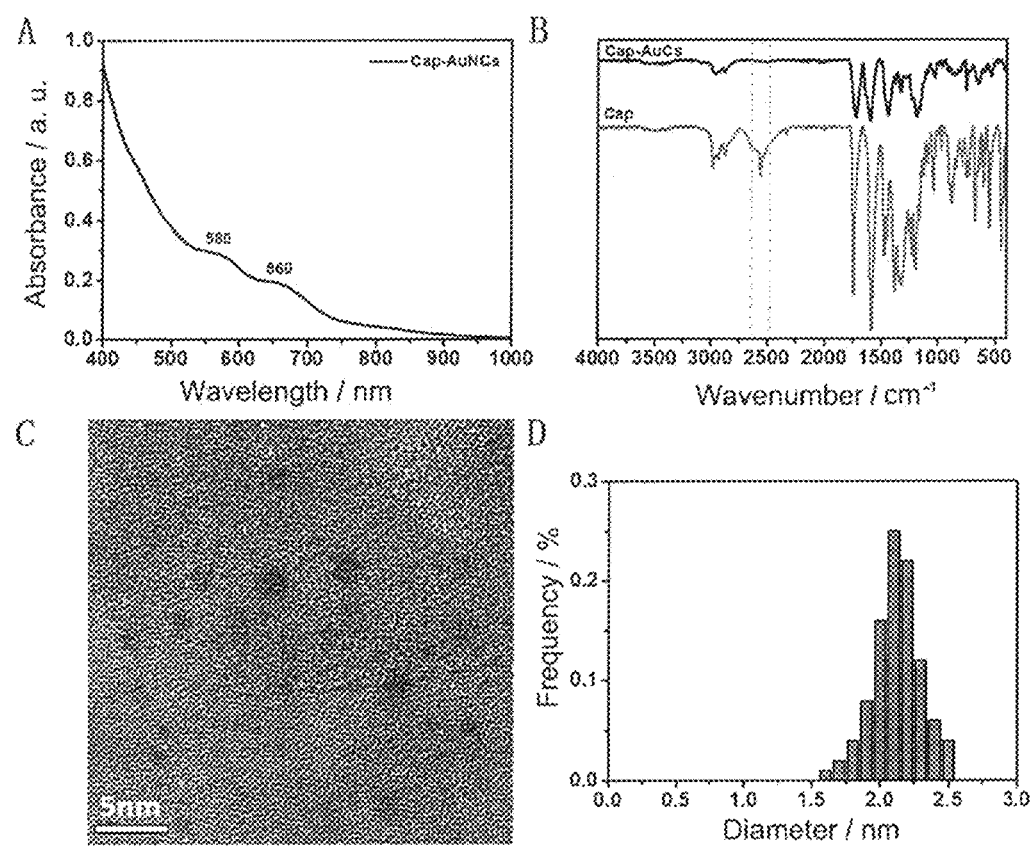
FIG. 6 shows UV, infrared, TEM, and particle size distribution diagrams of ligand 1-[(2S)-2-methyl-3-thiol-1-oxopropyl]-L-proline (i.e., Cap)-modified gold clusters (Cap-AuCs).
Figure 7:
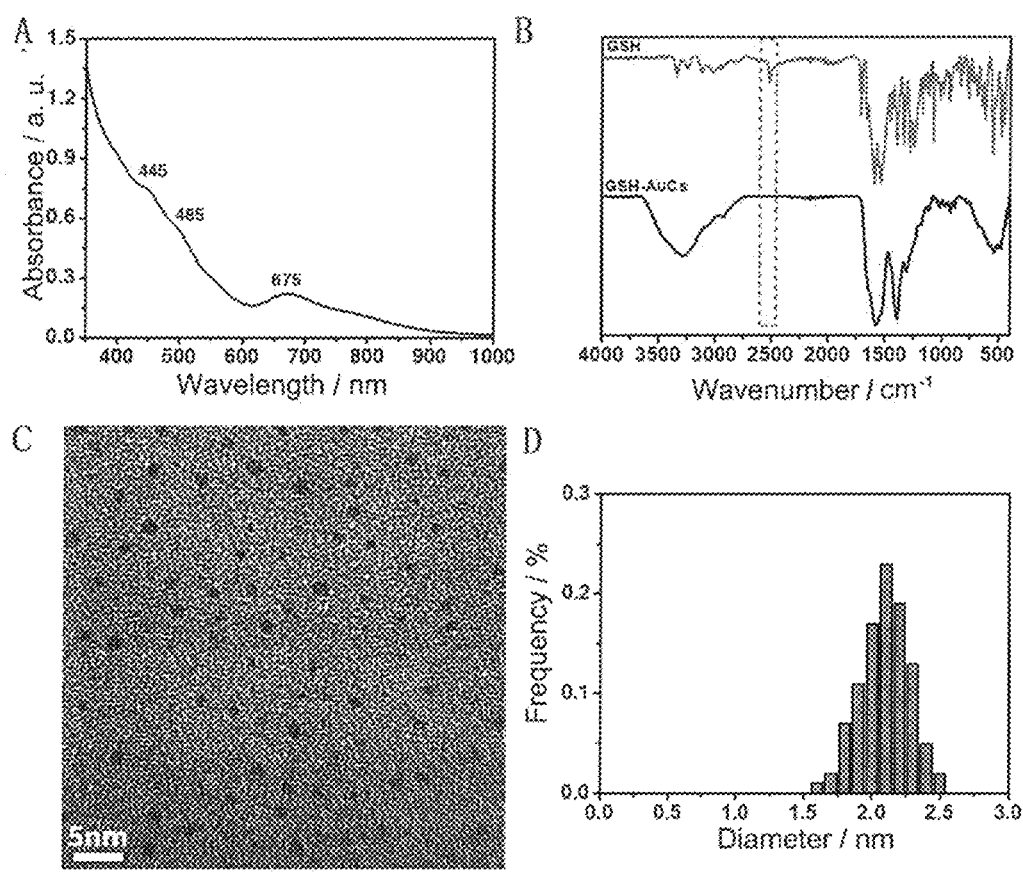
FIG. 7 shows UV, infrared, TEM, and particle size distribution diagrams of ligand GSH-modified gold clusters (GSH-AuCs).
Figure 8:
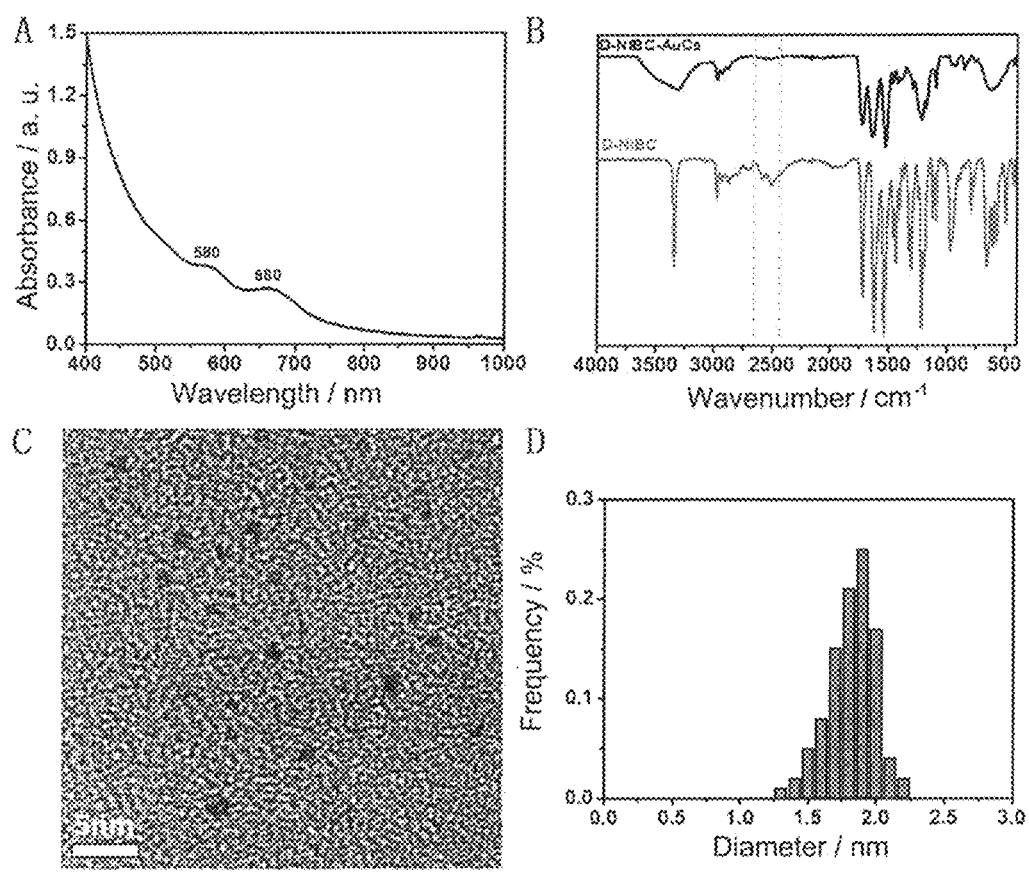
FIG. 8 shows UV, infrared, TEM, and particle size distribution diagrams of ligand D-NIBC-modified gold clusters (D-NIBC-AuCs).

The samples listed in Table 1 are confirmed by the foregoing methods. The characteristics of five different ligand-modified AuCs are shown in FIG. 4 (CR-AuCs), in FIG. 5 (RC-AuCs), in FIG. 6 (Cap-AuCs) (Cap denotes 1-[(2S)-2-methyl-3-thiol-1-oxopropyl]-L-proline), in FIG. 7 (GSH-AuCs), and in FIG. 8 (D-NIBC-AuCs). FIG. 4-FIG. 8 show UV spectra (panel A), infrared spectra (panel B), TEM images (panel C), and particle size distribution (panel D).

The results indicate that the diameters of AuCs modified with different ligands obtained from Table 1 are all smaller than 3 nm. Ultraviolet spectra also show disappearance of peak at 520±20 nm, and appearance of absorption peak above 560 nm. Only the position of this absorption peak varies slightly with ligand and particle size. Meanwhile, Fourier transform infrared spectra also show the disappearance of ligand thiol infrared absorption peak (between the dotted lines in panel B of FIGS. 4-8), while other infrared characteristic peaks are all retained, suggesting that all ligand molecules have been successfully anchored to the surface of AuCs, and the present invention has successfully obtained AuCs modified with the ligands listed in Table 1.

Embodiment 3

3.1 Materials and animals
3.1.1 Testing Sample
3.1.1.1 L-NIBC-AuCs with a core diameterf 1.5 nm was synthesized following the protocol hereinbelow 0.5 volume 5 g/L $HAuCl_4$ methanol solution was added into the reaction vessel to pre-cool it to 0° C. without light. Then, the $HAuCl_4$ methanol solution was kept at 0° C. and stirred slowly. 0.05 volume acetic acid (above analytical purity) and 0.1 volume 40 g/L N1BC methanol solution were added sequentially. After 1 hour of reaction, the rotating speed was increased, and 0.3 volume 15 g/L $NaBH_4$ ethanol solution was added. The solution was continued to react for 30 minutes, then the reaction was terminated by adding sufficient acetone. The solution was then centrifuged at 4000 r/min for 10 minutes. The supernatant was removed to collect the lower solid sediment. Then the solid sediment was added with 1 volume of 30 g/L ofNIBC aqueous solution, which was dissolved and sealed for ageing. After ageing for 24 hours, the solution was centrifuged at 4000 r/min for 10 minutes to remove the sediment, and the supernatant was put into a dialysis bag with a molecular weight of 3000, which was placed in ultrapure water for dialysis. After 5 times of dialysis, the solution in the dialysis bag was taken out and lyophilized into powder for being used as test sample. The test sample had a diameter of 1.5 nm with a spherical shape as shown in the TEM image (FIG. 2K). The UV-vis absorption spectrum of the test sample is shown FIG. 2J, and the statistical distribution of particle size is shown in FIG. 2L.

3.1.1.2 Specification: 25 mg/vial;
3.1.1.3 Traits: Taupe powder;
3.1.1.4 Storage conditions: 28° C. Confined dry preservation;
3.1.2 Positive control sample
3.1.2.1 Name: Pioglitazone hydrochloride tablets;
3.1.2.2 Batch Number: 1809001;
3.1.2.3 Traits: White or like white piece;
3.1.2.4 Specification/Purity: Pioglitazone 15 mg;
3.1.2.5 Packaging: Aluminum plastic packaging, 7pieces/box;
3.1.2.6 Production Date; 20180901:
3.1.2.7 Valid Until: 202108;
3.1.2.8 Producer: Yantai Zhengfang Pharmaceutical Co., Ltd.;
3.1.2.9 Clinical dose or recommended dose for human: The initial dose can be 15 mg or 30 mg once a day. If the initial dose is not well responded, add up to 45 mg once a day.
3.1.2.10 Storage Conditions: Covering, sealing.
3.1.3 Instruments
3.1.3.1 Electronic analytical balance (Shanghai Yousheng Weighing Apparatus Co., Ltd.; Sartorius Scientific Instruments (Beijing) Technology Co., Ltd.);
3.1.3.2 Blood glucose meter and blood glucose test strip (Johnson & Johnson),
3.1.3.3 LEICA® automatic dehydrator ASP300S;
3.1.3.4 LEICA® Biological Tissue Embedding Machine EG1150;
3.1.3.4 LEICA® Rotary Slicer Model RM2235;
3.1.3.5 LEICA® Spreader HI1210;
3.1.3.6 LEICA® Dryer HI1220;
3.1.3.7 LEICA® Automatic Dyeing Machine AutoStainer-XL;
3.1.3.8 OLYMPUS® Biological Microscope BX43;
3.1.3.9 OLYMPUS® microscopic image software CellSens Dimension;
3.1.3.10 Image-Prot Image Analysis Software Image-Pro Plus version 6.0.
3.1.4 Reagents
3.1.4.1 Sodium Chloride solution (Guangdong Kelun Pharmaceutical Co., Ltd.);
3.1.4.2 Sodium Carboxymethyl Cellulose (Tianjin Fuchen Chemical Reagent Factory); accurately weighed 5.0 g CMC-Na, slowly added into 800 mL of purified water in a beaker with stirring by a magnetic stirrer, until dissolved; 2~8° C. overnight; diluted to 1000 mL the next day; and store at 2~8° C. for later use;
3.1.4.3 Glucose (Guangdong Guanghua Technology Co., Ltd.); 0.25 g/mL glucose solution was prepared by adding 7.5 g of glucose into purified water to a final volume of 30 mL; 0.125 g/mL glucose solution was prepared by adding 7.5 g of glucose into purified water to a final volume of 60 mL;
3.1.4.4 Streptozotocin (STZ) (MP Bio company); 5 mg/mL STZ application solution was prepared by dissolving 0.15 g STZ into 30 mL of 0.1 mol/L citrate buffer;
3.1.4.5 Citric acid monohydrate, anhydrous ethanol, 95% ethanol (Guangdong Guanghua Technology Co., Ltd.); sodium citrate (Guangzhou Zhongnan Chemical Reagent Co., Ltd.); 0.1 mol/L citrate buffer was prepared as follows: adding 2.1 g of citric acid monohydrate into deionized water to a final volume of 100 mL, which is liquid A; adding 2.94 g of sodium citrate into deionized water to a final volume of 100 mL, which is liquid B; when used, mixed A and B in a ratio of 1:1~1.2; adjusted pH to 4.2~4.5; stored at 2~8° C.
3.1.4.6 Paraffin (Maoming Dachuan Special Wax Factory Co., Ltd.);
3.1.4.7 Transparent agent (Shanghai Hongzi Industrial Co., Ltd.);
3.1.4.8 Blush (water soluble) (Shanghai Aladdin Biochemical Technology Co., Ltd.); and
3.1.4.9 Su Musu (Shanghai Aladdin Biochemical Technology Co., Ltd).
3.2 Animal Experiment
3.2.1 C57BL/6 mice are more commonly used in diabetes tests. 90 C57BL/6 male mice (SPF level) with a body weight of 18.8-24.2 g at the beginning of the experiment were purchased from Guangdong Medical Laboratory Animal Center (Experimental Animal Production License No. SCXK (Yue) 2018-0002; Animal Certificate No. 44007200059759);

3.2.2 The content and procedures related to animal testing are in compliance with the relevant laws and regulations governing the use and management of laboratory animals and the relevant provisions of the Institutional Laboratory Animal Ethics Committee to ensure animal welfare;

3.2.3 At the end of the experiments, mice were injected intraperitoneally with sodium pentobarbital solution in an amount of 1 mL/kg body weight, and the eyeballs and bloods were collected, and then sacrificed by cervical dislocation;

3.2.4 Mice were quarantined for 4 days with daily inspection;

3.2.5 Mice were housed in single cage with 12 h: 12 h day/nighttime lighting; the room condition was always stable to ensure the reliability of the test results. Mice were free to eat and drink during the experiments.

3.2.6 Dose Design and Grouping 3.2.6.1 Dosage design: The dose of the test sample is 10 mg/kg body weight. The clinical dose of pioglitazone hydrochloride tablets is 45 mg/day for human, i.e. 0.75 mg/kg body weight based on average adult 60 kg bodyweight; the test dose is 30 times of human clinical dose; thus, the positive control group was administered at a dose of 22.5 mg/kg bodyweight;

3.2.6.2 Grouping: After the end of animal quarantine, fasting for about 5 h, tail blood was taken, blood glucose level (0 hours) was measured, and 0.25 g/mL glucose solution was administered at 10 mL/kg body weight, and the blood glucose level was measured at 0.5 hour. Six mice with too high or too low blood glucose levels were eliminated. The remaining mice were divided into negative control group, model control group, positive control group and sample group at 12 mice./group (Table 2).

Table 2. Grouping of Mice

TABLE 2

Dose design and grouping

| Group | n | Dose (mg/kg bodyweight) | Dosing volume and frequency |
|---|---|---|---|
| Negative control group | 12 | — | Intraperitoneal injection 20 mL/kg bodyweight, 1 time/day |
| Model control group | 12 | — | Intraperitoneal injection 20 mL/kg body weight, 1 time/day |
| Positive control group | 12 | 22.5 | Stomach 20 mL/kg body weight, 1 time/day |
| Sample group | 12 | 10 | Intraperitoneal injection 20 mL/kg body weight, 1 time/day |

3.2.7 Methods 3.2.7.1 High energy feed

Lard 10%, sucrose 15%, egg yolk powder 15%, casein 5%, cholesterol 1.2%, sodium cholate 0.2%, calcium hydrogen phosphate 0.6%. stone powder 0.4%, mouse maintenance material 52.6%.

3.2.7.2 Sample preparations: Test sample of the present invention was prepared by adding sodium chloride injection solution into the sample vial to obtain a concentration of 0.5 mg/mL; then stored at 2~8° C., shaded from light. Positive control sample was prepared by mixing 1 tablet of pioglitazone hydrochloride (specification 15 mg/tablet) with 0.5% CMC-Na solution and grinded it evenly, then added 0.5% CMC-Na solution to a final volume of 13.3 mL, and shook well prior to use.

3.2.7.3 Establishing diabetic model

After each group was given a maintenance feed for 1 week, except for the negative control group, the other groups were replaced with the high energy feed from 3.1.7.1. After 3 weeks of feeding, each group was fasted for 24 h. Except for the negative control group, the other groups were intraperitoneally injected with 5 mg/mL STZ solution at a dose of 20 mL/kg bodyweight. All groups were fed for 4 days. Fasting blood glucose and glucose tolerance were measured on the 5th day, and the test was terminated the next day.

3.2.7.4 Administration of test sample and positive control sample

From the feeding of the maintenance feed, the sample group was intraperitoneally injected with the test sample solution once per day at 20 mL/kg bodyweight, the negative control group and the model control group were intraperitoneally injected with sodium chloride solution, and the positive control group was intragastrically administered with pioglitazone hydrochloride solution at a dose of 20 mL/kg bodyweight for 34 days until the end of the test. On the day of injection of STZ, each group was administered 4 h after STZ injection.

3.2.7.5 The measurement of the last fasting blood glucose and glucose tolerance, and material extraction On the 5th day after intraperitoneal injection of STZ, the mice in each group were fasted for about 5 hours with water provided. After measuring the fasting blood glucose level (0 h), the sample group and positive control group were intraperitoneally injected with the corresponding drugs. The negative control group and the model control group were intraperitoneally injected with sodium chloride solution. After 20 minutes, each group was intragastrically administered with 0.125 g/mL glucose solution at 20 mL/kg bodyweight, and the blood glucose level was measured at 0.5, 1, 1.5, 2 h after the administration of the glucose solution. On the next day, the mice in each group were fasted for 5 h after the administration. The mice were anesthetized with 3% sodium pentobarbital solution in an amount of 10 mL/kg bodyweight, and sacrificed after collecting the eyeballs and bloods. The blood samples were centrifuged at 3000 r/min for 10 min, and the sera were collected for the detection of serum insulin, triglycerides, and total cholesterol. At the same time, the pancreas of each animal was collected. Six animals in each group were fixed with 10% paraformaldehyde for HE staining and insulin immunohistochemical staining in pancreas. The remaining 6 animals were preserved at −80° C. for insulin content determination.

3.2.8 Detection Indicators 3.2.8.1 General clinical observation

The general clinical condition of the animals was observed once a day until the end of the trial.

3.2.8.2 Bodyweight

Weighed at the beginning of the trial, at the end of the trial, and once a week during the trial.

3.2.8.3 Feed intake

Each week, the animals' feed intake in two days was measured once by weighing the added feed, and the remaining feed the next day.

3.2.8.4 Blood glucose drop rate

Blood glucose drop rate=(blood glucose value prior to experiment−blood glucose value post experiment)/(blood glucose value prior to experiment)×100% .

3.2.8.5 Area under the glucose tolerance blood glucose curve

Calculate the area under the blood glucose curve at 0, 0.5, 1, 1.5, 2 h after glucose administration. The formula is as follows:

Area under the blood glucose curve: [(0 h blood glucose+ 0.5 h blood glucose)×0.5]/2+[(0.5 h blood glucose+1 h blood glucose)×0.5]/2+[(1 h blood glucose+1.5 h) Blood glucose level)×0.5]/2+[(1.5 h blood glucose level+2 h blood glucose value)×0.5]/2.

3.2.8.6 Serum insulin, cholesterol, and triglycerides

At the end of the experiment, serum was collected for assaying serum insulin, triglycerides, and total cholesterol. The insulin resistance index was calculated.

Insulin resistance index=insulin/$22.5e^{-inBlood\ glucose}$ 3.2.8.7 HE staining After the pancreas from 6 animals in each group were fixed with 10% paraformaldehyde, the islet inflammation vas observed by HE staining, and semi-quantitative rating was performed on the scale of 0–4.

0: No pathological changes;
1: Peripheral islet inflammation: signs of pathological infiltration, pathological changes are limited to the periphery of the islets;
2: mild islet inflammation: less than 25% of islets show pathological infiltration changes;
Moderate islet inflammation: 25% to 75% of islets show pathological infiltration changes;
4: severe islet inflammation: more than 75% of islets show pathological infiltration changes.

3.2.8.8 Immunohistochemistry

10% paraformaldehyde-fixed pancreatic tissues were used for immunohistochemistry to detect insulin expression.

3.2.8.9 Determination of insulin content in pancreatic tissue

Pancreatic tissue of the remaining 6 animals in each group was stored at 80° C. for ELISA to detect insulin content the pancreas.

3.2.9 Evaluation of results 3.2.9.1 The conditions for establishing the glucose metabolism disord.er model 3.2.9.2 Fasting blood glucose index Under the premise of the establishment of the glucose metabolism disorder model, compared with the model control group, the fasting blood glucose decreased or the percentage of blood glucose decreased was statistically significant, and the fasting blood glucose index of the test sample as positive.

3.2.9.3 Glucose tolerance index

Under the premise of the establishment of the glucose metabolism disorder model, compared with the model control group, the test sample group was statistically significant at 0, 1, 1.5, and 2 h after the glucose solution was administered, or the area under the blood glucose curve of 0, 0.5, 1, 1.5, and 2 h was statistically significant, so the glucose tolerance index of the test sample was positive.

3.2.10 Statistic analyses

All data were expressed by ($\bar{x}\pm s$), using SPSS 21.0 software for statistical analysis; body weight, food intake, fasting blood glucose after test, glucose tolerance using repeated measures analysis of variance; fasting blood glucose, TC content, insulin, pancreatic insulin using analysis of variance after log conversion. The average optical density of pancreatic insulin was measured by T test; percentage of blood glucose drop, area under blood glucose curve, TG content were analyzed by rank sum test; and the statistical analysis of islet inflammation score using chi-square test. The test level is $\alpha=0.05$, and the chi-square test level is corrected to $\alpha=0.0024$.

3.3 Results 3.3.1 Observation

There was no abnormality in the general clinical situation and the second stools of the animals before the intraperitoneal injection of STZ. After the intraperitoneal injection of STZ, the body weight decreased.

3.3.2 Body weight

There was no statistical difference in body weight between the groups during the trial (Table 3).

TABLE 3

Body weight of all groups of mice during experiments

| Group | Dose mg · kg$^{-1}$ · d$^{-1}$ | n | Bodyweight (g) | | | | | | |
|---|---|---|---|---|---|---|---|---|---|
| | | | d 2 | d 9 | d 16 | d 23 | d 29 | d 32 | d 35 |
| Negative control | — | 12 | 22.4 ± 1.0 | 22.9 ± 1.2 | 25.0 ± 1.5 | 26.5 ± 1.5 | 26.9 ± 1.7 | 27.7 ± 1.7 | 27.8 ± 1.9 |
| Model control | — | 12 | 22.7 ± 1.0 | 23.6 ± .1.1 | 25.6 ± 1.3 | 26.6 ± 1.4 | 27.4 ± 1.7 | 26.4 ± 1.7 | 26.6 ± 1.7 |
| Positive control | 22.5 | 12 | 22.2 ± 1.2 | 23.0 ± 1.3 | 24.2 ± 1.2 | 25.6 ± 1.5 | 26.2 ± 1.6 | 26.0 ± 1.4 | 25.8 ± 1.3 |
| Sample | 10 | 12 | 22.7 ± 1.3 | 23.5 ± 1.4 | 24.4 ± 1.4 | 25.6 ± 1.1 | 26.3 ± 1.2 | 25.7 ± 1.3 | 26.0 ± 1.1 |

The model control group had a blood glucose level≥10 mmol/L at 0.5 h, or the blood glucose level or the area under the blood glucose curve at any time point at 0.5, 1, 1.5, and 2 h had a statistically significant increase over the negative control group.

3.3.3 Food intake

Compared with the model control group, the positive control group increased food intake at week 1, and the sample group increased food intake at week 1 but decreased food intake at week 2 and week 5 (Table 4).

TABLE 4

Food intake of all groups of mice

| Group | Dose mg · kg$^{-1}$ · d$^{-1}$ | n | Food Intake (g/mouse · d$^{-1}$) | | | | |
|---|---|---|---|---|---|---|---|
| | | | Week 1 | Week 2 | Week 3 | Week 4 | Week 5 |
| Negative control | — | 12 | 6.4 ± 0.4 | 6.2 ± 0.6 | 7.1 ± 0.4 | 7.1 ± 0.4 | 9.8 ± 0.6 |
| Model control | — | 12 | 6.6 ± 0.4 | 7.1 ± 0.4▲▲ | 7.3 ± 0.6 | 7.3 ± 0.6 | 9.3 ± 0.7 |

TABLE 4-continued

Food intake of all groups of mice

| Group | Dose mg · kg⁻¹ · d⁻¹ | n | Food Intake (g/mouse · d⁻¹) | | | | |
|---|---|---|---|---|---|---|---|
| | | | Week 1 | Week 2 | Week 3 | Week 4 | Week 5 |
| Positive control | 22.5 | 12 | 7.3 ± 0.3** | 6.8 ± 0.3 | 7.5 ± 0.3 | 7.6 ± 0.4 | 8.6 ± 0.6 |
| Sample | 10 | 1 | 7.0 ± 0.4* | 6.6 ± 0.5* | 7.1 ± 0.4 | 7.0 ± 0.7 | 8.1 ± 1.4** |

3.3.4 Fasting blood glucose index

Compared with the negative control group, the model control group had increased fasting blood glucose level. The value of the increased percentage of fasting blood glucose level was negative and statistically significant compared with the negative control group ($P<0.05$). Compared with the model control group, the fasting blood glucose levels of the sample group and the positive control group decreased significantly ($P<0.05$).

TABLE 5

Fasting blood glucose index of all groups of mice

| Group | Dose g · kg⁻¹ · d⁻¹ | n | Fasting blood glucose index (mmol/L) | | |
|---|---|---|---|---|---|
| | | | Prior to Experiment | Post experiment | Decrease percentage of blood glucose (%) |
| Negative control | — | 12 | 11.5 ± 1.2 | 10.3 ± 1.9 | 9.9 ± 16.2 |
| Model control | — | 12 | 11.7 ± 1.4 | 18.3 ± 5.6▲▲ | −61.2 ± 57.4▲ |
| Positive control | 22.5 | 12 | 12.0 ± 2.6 | 13.8 ± 2.8* | −21.8 ± 39.0 |
| Sample | 10 | 12 | 11.7 ± 2.1 | 12.5 ± 5.8* | −12.5 ± 64.9 |

3.3.5 Glucose tolerance index

Compared with the negative control group, the blood glucose level of the model control group at 0.5 h, 1 h, 1.5 h, 2 h, and the area under the blood glucose curve were statistically significant ($P<0.01$), and the model of glucose metabolism disorder was established. Compared with the model control group, the blood glucose levels in the sample group at 0.5 h, 1 h, 1.5 h, and 2 h were statistically significant ($P<0.05$ or $P<0.01$).

TABLE 6

Glucose tolerance index of all groups of mice

| Group | Dose g · kg⁻¹ · d⁻¹ | Glucose tolerance index (mmol/L) | | | | | area under the blood glucose curve |
|---|---|---|---|---|---|---|---|
| | | 0 h | 0.5 h | 1 h | 1.5 h | 2 h | |
| Negative control | — | 10.3 ± 1.9 | 15.2 ± 4.3 | 12.1 ± 1.4 | 11.4 ± 2.3 | 9.3 ± 1.3 | 24.2 ± 3.1 |
| Model control | — | 18.3 ± 5.6▲▲ | 31.5 ± 2.4▲▲ | 27.6 ± 3.9▲▲ | 24.8 ± 4.3▲▲ | 22.9 ± 4.7▲▲ | 52.2 ± 6.8▲▲ |
| Positive control | 22.5 | 13.8 ± 2.8* | 30.1 ± 5.4 | 26.9 ± 7.0 | 20.7 ± 6.2 | 17.9 ± 6.3* | 46.8 ± 10.1 |
| Sample | 10 | 12.5 ± 5.8* | 23.3 ± 7.8** | 18.0 ± 8.6** | 15.8 ± 7.6** | 12.9 ± 6.4** | 34.9 ± 14.4 |

3.3.6 Serum insulin content

Compared with the negative control group, the serum insulin content in the model control group decreased statistically ($P<0.01$). Compared with the model control group, the serum insulin content in the positive control group increased statistically ($P<0.05$).

3.3.7 Pancreatic insulin content

Compared with the negative control group, the pancreatic insulin content in the model control group decreased statistically ($P<0.01$). Compared with the model control group, the pancreatic insulin content in the positive control group increased, but without significance ($P>0.05$).

3.3.8 Cholesterol (TC) content

Compared with the negative control group, the TC content in the model control group increased statistically ($P<0.01$); compared with the model control group, the TC content in the sample group decreased statistically ($P<0.01$).

3.3.9 Triglyceride (TG) content

Compared with the negative control group, the TG content of the model control group increased, but there was no statistical significance ($P>0.05$). The TG content of the positive drug group and the sample group decreased, but without significance ($P>0.05$).

TABLE 7

TC, TG, serum insulin content, and pancreatic insulin content of all groups of mice

| Group | Dose g · kg$^{-1}$ · d$^{-1}$ | TC (mmol/L) | TG (mmol/L) | serum insulin content (mIU/mL) | pancreatic insulin content (mIU/mL) |
| --- | --- | --- | --- | --- | --- |
| Negative control | — | 2.65 ± 0.23 | 0.85 ± 0.11 | 29.6 ± 2.5 | 12.6 ± 4.3 |
| Model control | — | 4.94 ± 0.69▲▲ | 1.01 ± 0.40 | 24.8 ± 4.8▲▲ | 7.3 ± 2.9▲▲ |
| Positive control | 22.5 | 4.76 ± 0.56 | 0.76 ± 0.14 | 28.2 ± 3.6* | 8.4 ± 3.0 |
| Sample | 10 | 3.90 ± 0.65** | 0.79 ± 0.17 | 23.9 ± 3.7 | 7.0 ± 2.4 |

3.3.10 HE staining results

Figure 9:
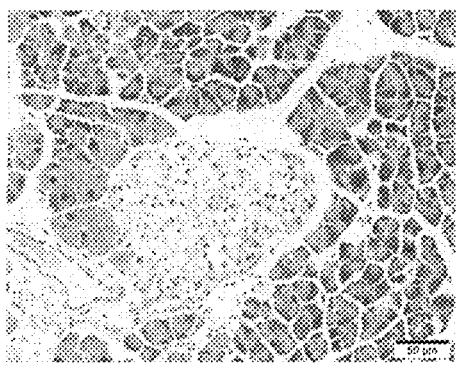
FIG. 9 shows the HE staining results of pancreases; (a) negative control group; no abnormal changes; (b) model control group; severe decreases of islet numbers, islet volumes and islet cell numbers, and apparent lymphocyte infiltration into islets; (c) positive control group; moderate decreases of islet numbers, islet volumes and islet cell numbers, and apparent lymphocyte infiltration into islets; (d) sample group; no apparent decreases of islet numbers, islet volumes and islet cell numbers, and no lymphocyte infiltration into islets.
Figure 9:
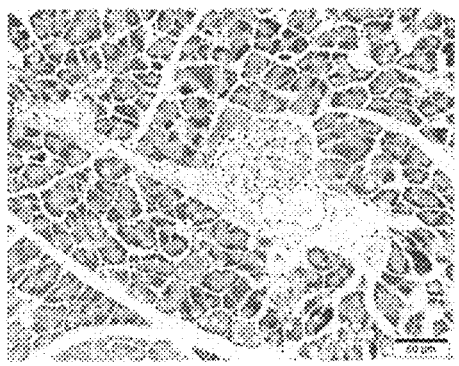
Figure 9:
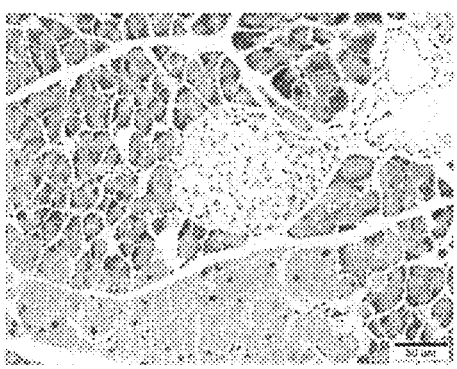
Figure 9:
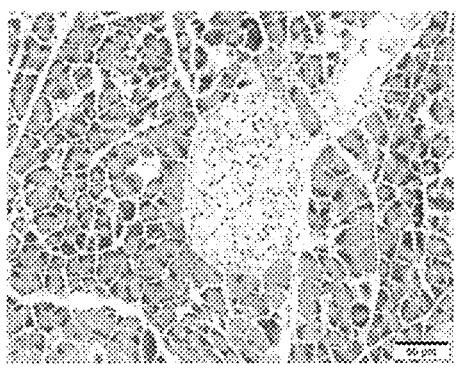

Compared with the negative control group (FIG. 9(a)), the model control group showed severe decreases of islet numbers, islet volumes and islet cell numbers, and apparent lymphocyte infiltration into islets (FIG. 9(b)), the positive control group showed moderate decreases of islet numbers, islet volumes and islet cell numbers, and apparent lymphocyte infiltration into islets (FIG. 9(c)), but the sample group showed no apparent decreases of islet numbers, islet volumes and islet cell numbers, and no lymphocyte infiltration into islets (FIG. 9(d)).

3.3.11 Insulin immunohistochemistry results

Figure 10:
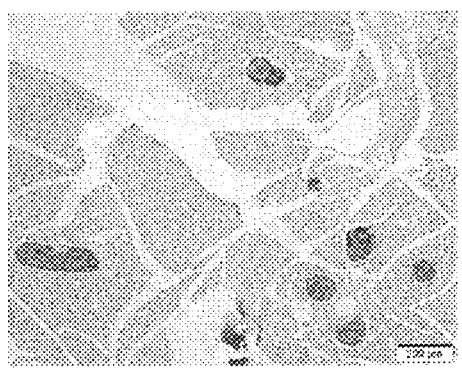
FIG. 10 shows the results of insulin immunohistochemistry in the pancreases; (a) negative control group; normal insulin-positive islets; (b) model control group; severe decrease of insulin-positive islets; (c) positive control group; significant decrease of insulin-positive islets; (d) sample group; no apparent decrease of insulin-positive islets.
Figure 10:
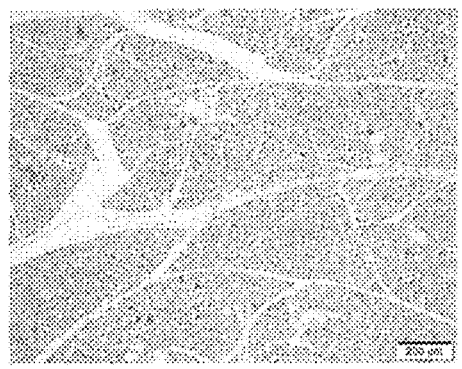
Figure 10:
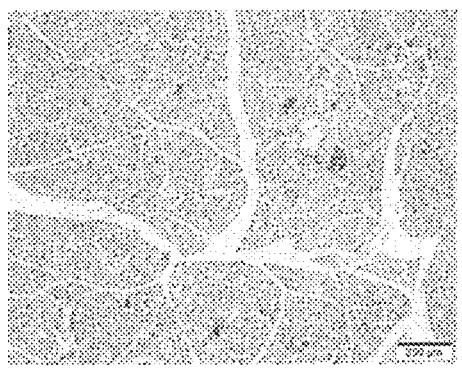
Figure 10:
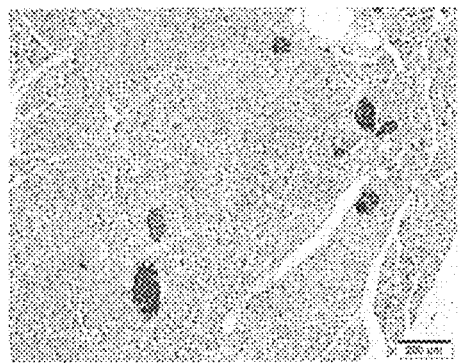
Figure 11:
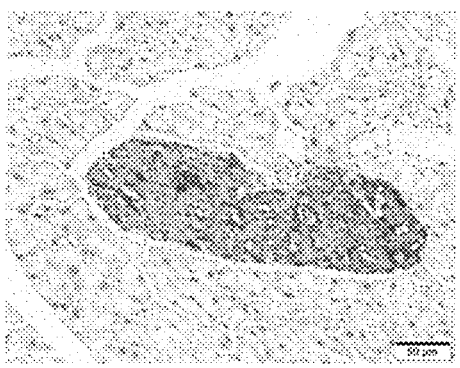
FIG. 11 shows the results of insulin immunohistochemistry in the islets; (a) negative control group; normal number of insulin-positive cells; (b) model control group; severe decrease of the number of insulin-positive cells; (c) positive control group; significant decrease of the number of insulin-positive cells; (d) sample group; no apparent decrease of the number of insulin-positive cells.
Figure 11:
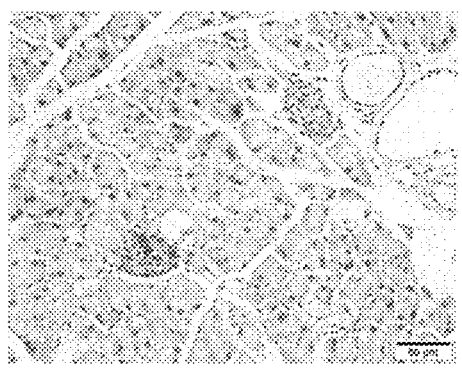
Figure 11:
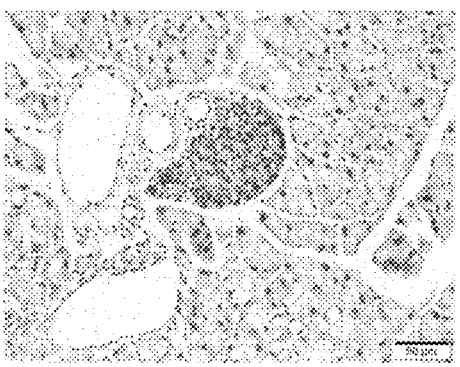
Figure 11:
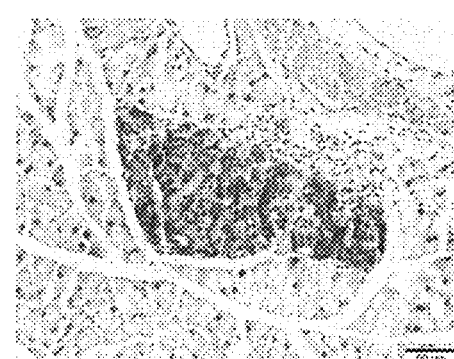

Compared with the negative control group (FIG. 10(a) and FIG. 11(a)), the model control group showed severe decreases of insulin-positive islets and pancreatic cells (FIG. 10(b) and FIG. 11(b)), the positive control group showed significant decreases of insulin-positive islets and pancreatic cells (FIG. 10(c) and FIG. 11(c)), but the sample group showed no apparent decreases of insulin-positive islets and pancreatic cells (FIG. 10(d) and FIG. 11(d)).

Embodiment 4

4.1 Reagents

Cholesterol test kit, LabAssay™ Cholestro, Baobai Bio/Wako

Triglyceride detection kit, LabAssay Triglyceride, Baobai Bio/Wako

Free fatty acid detection kit, LabAssay NEFA, Baobai Bio/Wako

Glucose test kit, LabAssay Glucose, Baobai/Wako

Insulin test kit, Rat/Mouse Insulin ELISA, Shanghai Jifeng/Millipore

GOT, GPT kit, Nanjing Jiancheng Biology Co., Ltd

Reverse transcription reagent, Novozan

Hieff™ qPCR SBYR Green Mastey Mix, Eason Biotechnology (Shanghai) Co., Ltd

High fat diet, Research Diet, Catalog no. D12492

4.2 Test drug

A-03: L-NIBC-AuCs with a size of 0.5-2.6 nm 4.3 Animal test methods

Mouse model: B6 high-fat mouse model.

B6 mice were divided into five groups: normal control group (B6 mice were normally fed throughout the experiment); A-03 drug control group (B6 mice were normally fed throughout the experiment and injected intraperitoneally with A-03 high dose (10 mg/Kg mouse body weight) from 5-months old); the model control group (B6 mice were fed with high-fat diet from 2-months old and injected intraperitoneally with normal saline from 5-months old); the low dose group (B6 mice were fed with high-fat diet from 2-months old and injected intraperitoneally with A-03 low dose (1 mg/Kg mouse body weight) from 5-months old; the medium dose group (B6 mice were fed with high-fat diet from 2-months old and injected intraperitoneally with A-03 medium dose (5 mg/Kg mouse body weight) from 5-months old; and the high dose group (B6 mice were fed with high-fat diet from 2-months old and injected intraperitoneally with A-03 high dose (10 mg/Kg mouse body weight) from 5-months old.

4.4 Results 4.4.1 Establishment of diabetic mouse model

The obese mice model induced by high-fat diet was used to study the therapeutic effect of A-03 drug on diabetes.

Figure 13:
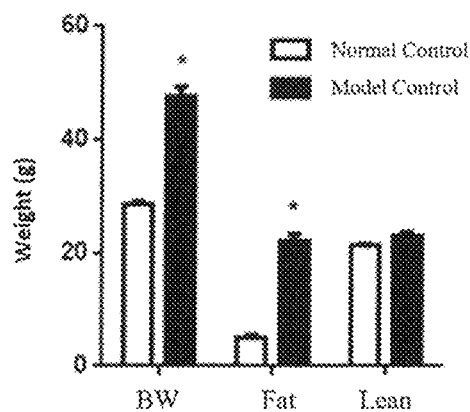
FIG. 13 shows comparison of normal control group with model control group: (a) differences in body weight, fat and lean meat weight of mice; (b) fasting blood glucose index and insulin hypoglycemic ability; (c) glucose tolerance index.
Figure 13:
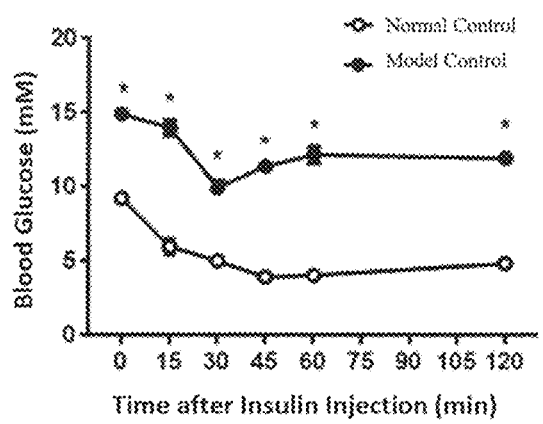
Figure 13:
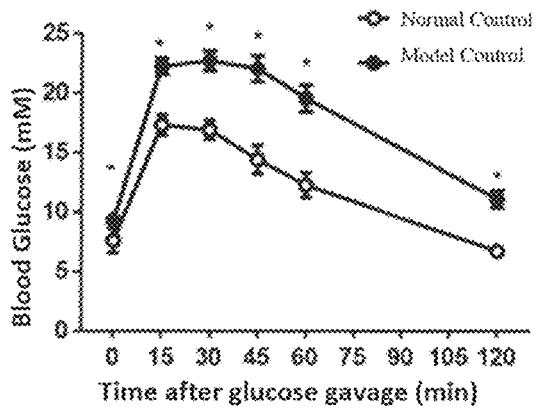

FIG. 13a shows the comparison of body weight, fat and lean meat weight between the normal control group and the model control group. Compared with the normal control group, the body weight and fat weight of the model control group were significantly increased ($P<0.05$, *), but the lean meat content had no significant change.

FIG. 13b shows the comparison of fasting blood glucose index and insulin hypoglycemic ability between the normal control group and the model control group (all with significant differences; $P<0.05$, *).

FIG. 13c shows the comparison of glucose tolerance indexes between the normal control group and the model control group (all with significant differences, $P<0.05$, *).

All the treatment groups were the same as the model control group. The results showed that the model was successfully established.

4.4.2 The effects of A-03 drug on blood glucose in diabetic mice

Two administration schemes were set up. The first was acute drug administration, i.e. the test was conducted immediately after 30 minutes of drug administration. The second was long-term drug administration, i.e. the drug was administered once a day for two consecutive months, and the test was conducted at 1 month and 2 months after administration.

4.4.2.1 Results of acute drug administration

Figure 14:
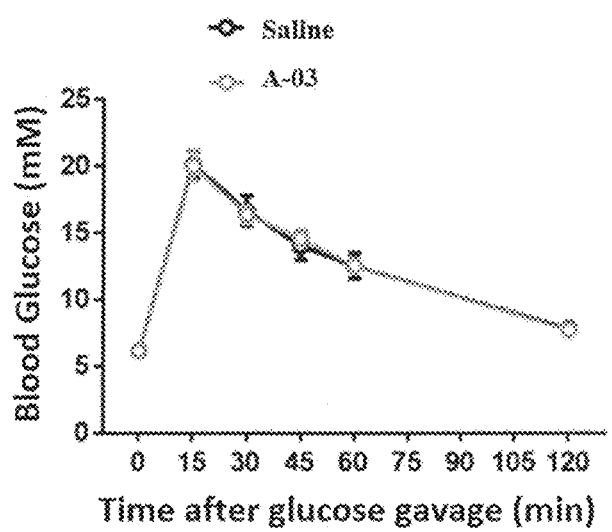
FIG. 14 shows the acute hypoglycemic effect of A-03 drug in: (a) normal mice; (b) model mice.
Figure 14:
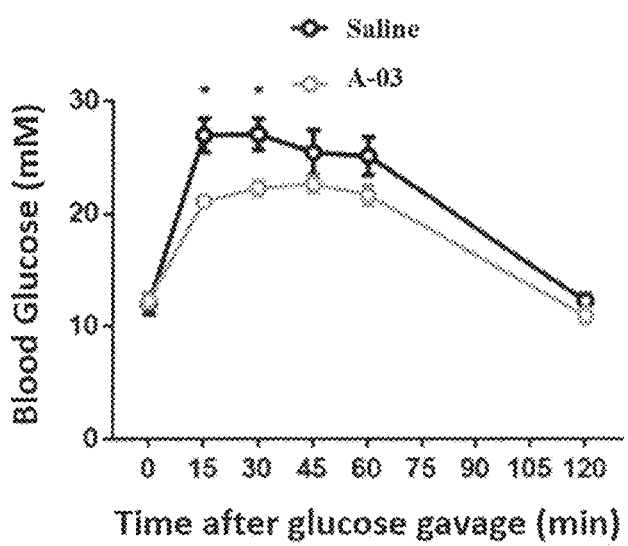

For normal mice and model mice, 30 minutes after acute administration of A-03 drug (10 mg/kg mouse body weight), the effect of A-03d drug on glucose tolerance was detected (injection of saline as control for both the normal and model mice). After 30 minutes of high-dose administration of A-03, the glucose tolerance of high-fat diet model mice was significantly improved (FIG. 14b, at 15 and 30 minutes, the blood glucose of A-03 high-dose administration group was significantly lower than that of normal saline control group, $P<0.05$, *), but there was no significant change in normal mice (FIG. 14a).

4.4.2.2 Results of long-term drug administration

Figure 15:
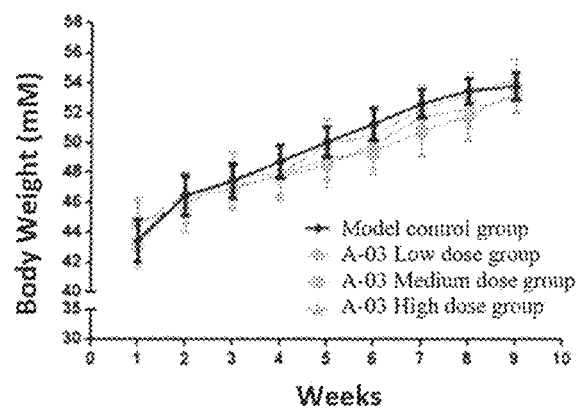
FIG. 15 shows the effects of A-03 drug on the model mice: (a) body weight; (b) fat, where (1) is the normal control group, (2) is the model control group, (3) is the A-03 medium dose administration group; (c) muscle tissue, where (1) is the normal control group, (2) is the model control group, and (3) is the A-03 medium dose administration group.
Figure 15:
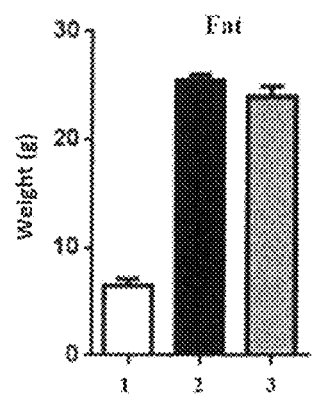
Figure 15:
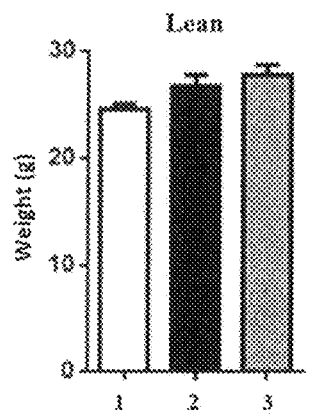

FIG. 15a shows the body weight changes of A-03 low, medium and high-dose administration groups compared with the model control group.

FIG. 15b and FIG. 15c show the effect of the exemplary medium dose A-03 drug on fat and lean meat, respectively.

In conclusion, compared with the model mice, long-term drug administration of three doses of A-03 has no significant impact on the weight and body fat ratio of the model mice. Therefore, drug toxicity is first excluded, and it can be explained that the use of drugs has no significant impact on the diet and metabolic consumption of mice.

Figure 16:
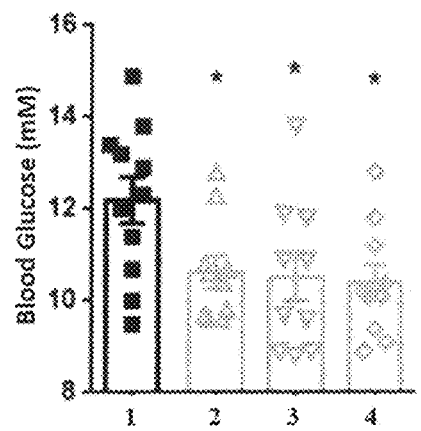
FIG. 16 shows the hypoglycemic effect of A-03 drug at one month after administration, where (1) is the model control group; (2) is the high-dose administration group; (3) is the medium dose administration group; and (4) is the low-dose administration group.

One month after administration, blood glucose of the model control group and each drug administration group was measured under the condition of random diet (no starvation). FIG. 16 shows that the three concentrations of A-03 drug have significant hypoglycemic effect ($P<0.05$, *).

Figure 17:
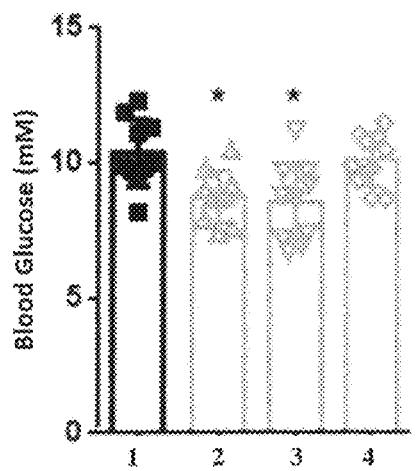
FIG. 17 shows the hypoglycemic effect of A-03 drug at two months of administration, where (1) is the model control group, (2) is the high-dose administration group, (3) is the medium dose administration group, and (4) is the low-dose administration group.

Two months after administration, fasting blood glucose of the model control group and each drug administration group was measured after starvation overnight. FIG. 17 shows that there is a significant control effect of A-03 drug on blood glucose ($P<0.05$, *).

These results indicate that A-03 drug has a significant inhibitory effect on blood glucose.

Figure 18:
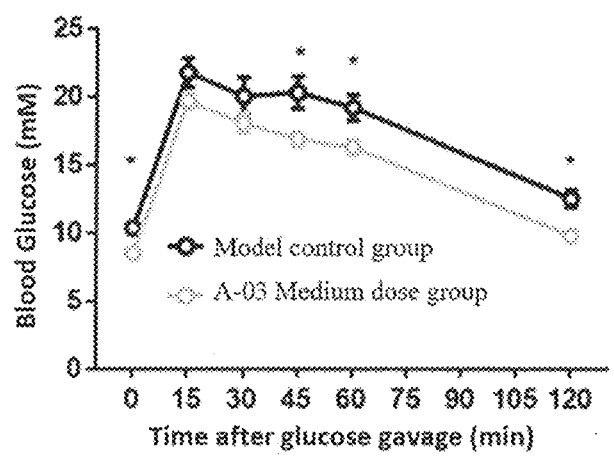
FIG. 18 shows the effect of A-03 drug on (a) glucose tolerance and (b) insulin hypoglycemic effect (* means $P<0.05$).
Figure 18:
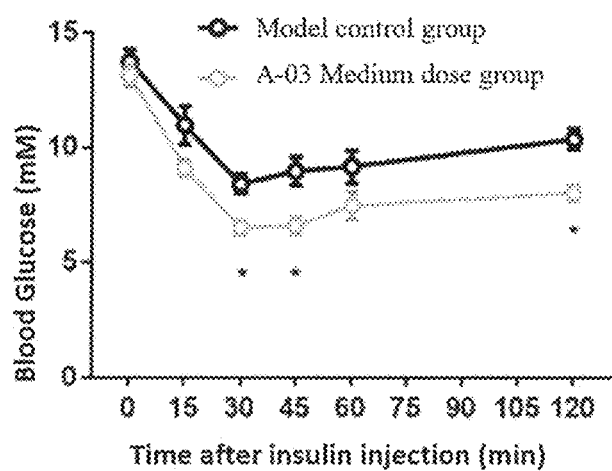

Further experiments showed that low, medium and high doses of A-03 drug could significantly improve glucose tolerance and insulin resistance induced by high-fat diet. FIG. 18 shows the effect of the exemplary medium dose A-03 drug on (a) glucose tolerance and (b) insulin hypoglycemic effect (* means $P<0.05$).

4.4.3 Effects of A-03 drug on plasma total cholesterol content in model mice

Figure 19:
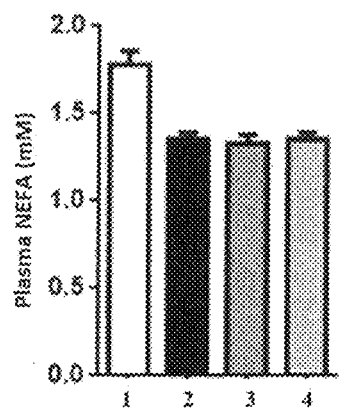
FIG. 19 shows the effects of medium and high doses of A-03 drug on blood lipid in model mice: (a) plasma non-esterified fatty acid content (plasma NEFA); (b) serum triglyceride (plasma TG); (c) serum total cholesterol (plasma TC), where (1) is the normal control group; (2) is the model control group; (3) is the A-03 medium dose administration group; (4) is the A-03 high-dose administration group.
Figure 19:
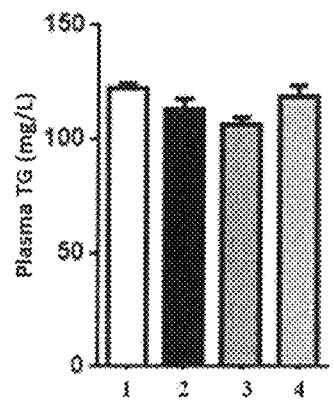
Figure 19:
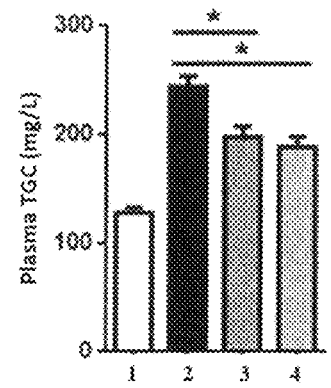

In addition to the hypoglycemic effect, we also found that blood lipids were significantly improved after drug treatment. Here the blood lipids refer to the serum total cholesterol, triglycerides and non-esterified fatty acids. FIG. 19 shows the effects of the medium and high dose A-03 drug on serum non esterified fatty acid content (FIG. 19a), serum triglyceride (FIG. 19b) and serum total cholesterol (FIG. 19c), where 1-4 represents the normal control group, the model control group, the A-03 medium dose administration group and the A-03 high-dose administration group, respectively. The A-03 medium and high doses had no significant effect on NEFA and TG, but decreased TC from 243.2±9.7 mg/dL (model control group) to 188.4±9.4 mg/dL and 197.1±10.4 mg/dL respectively, and the differences were significant ($P<0.05$, *).

4.4.4 Effects of A-03 drug on blood insulin content of model mice

Figure 20:
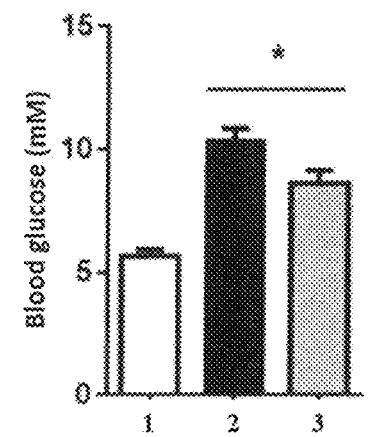
FIG. 20 shows the effects of A-03 medium dose administration on: (a) fasting blood glucose and (b) blood insulin content, where (1) is the normal control group; (2) is the model control group; and (3) is the A-03 medium dose administration group.
Figure 20:
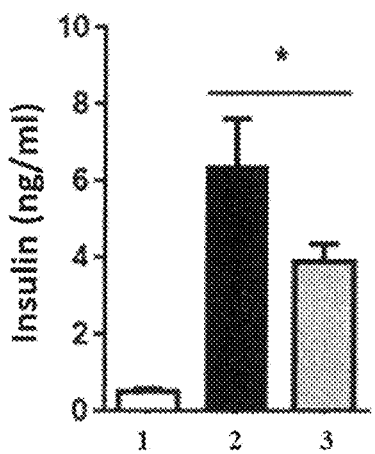

FIG. 20 shows the effects of A-03 drug after administration of medium dose drug for 2 months on blood glucose (FIG. 20a) and blood insulin content (FIG. 20b) in the model mice under fasting conditions, where 1-3 in the column graph represents the normal control group, the model control group, and the A-03 medium dose administration group, respectively. Fasting blood glucose decreased from 10.38±0.39 mm to 8.55±0.45 mm ($P<0.05$, *). The corresponding blood insulin content decreased from 6.03±0.85 ng/ml to 3.86±0.38 ng/ml ($P<0.05$, *).

4.4.5 Effects of A-03 drug on liver

Mice were fed and administered of A-03 drug following the long-term drug administration protocol described above, the period of drug administration was 2.5 months.

4.4.5.1 Effects on G6Pase, a key rate limiting enzyme of gluconeogenesis

Figure 21:
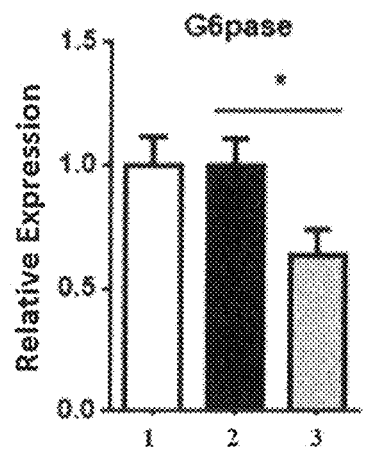
FIG. 21 shows the effect of A-03 medium dose administration on the liver of mice: (a) expression of glucose-6-phosphate dehydrogenase (G6Pase), where (1) is the normal control group, (2) is the model control group, (3) is the A-03 medium dose group; (b) the amount of liver glycogen, where (1) is the normal control group, (2) is the model control group, (3) is the A-03 medium dose group; (c) Expressions of key molecules in oxidative phosphorylation during glucose metabolism, where in each gene, the columns from left to right are the normal control group, the model control group and the A-03 medium dose group.
Figure 21:
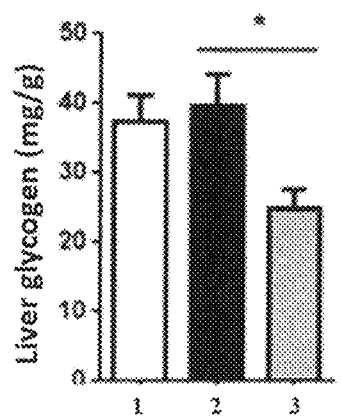
Figure 21:
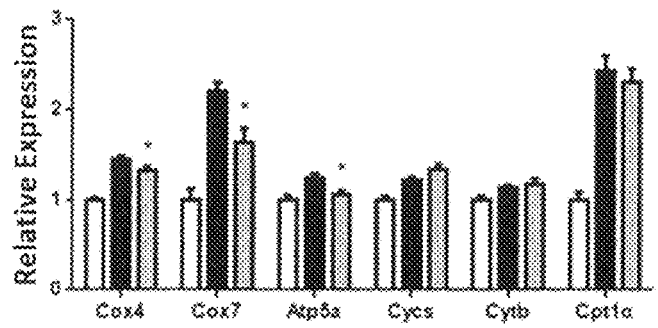

Gluconeogenesis is a process in which non-glucose precursors are converted into glucoses, mainly occurring in the liver. Glucose-6-phosphate dehydrogenase (G6Pase) is a key rate limiting enzyme of gluconeogenesis. The expression of G6Pase is directly correlated to the rate of glucose production. FIG. 21a shows that A-03 drug with an exemplary medium dose could significantly inhibit the gene expression of G6Pase ($P<0.05$, *), while FIG. 21b shows that glycogen content in liver is significantly reduced ($P<0.05$, *). FIG. 21C shows the effects on the expression of other key molecules of oxidative phosphorylation in glucose metabolism such as cytochrome c oxidase IV (Cox4), cytochrome c oxidase VII (Cox7), alpha peptide of mitochondrial F1 complex of hydrogen ion transport ATPase (Atp5a), cytochrome c (Cycs), cytochrome b gene (Cytb) in mitochondrial DNA and carnitine palmitoyltransferase 1A (Ctp1a).

It can be seen that oxidative phosphorylation did not increase, but Cox 4, Cox 7 and Atp5a decreased significantly ($P<0.05$, *), indicating that the decrease of blood glucose may be due to the effective drug control of gluconeogenesis in the liver, rather than the increase of consumption.

4.4.5.2 Effects on intrahepatic insulin sensitivity

Figure 22:
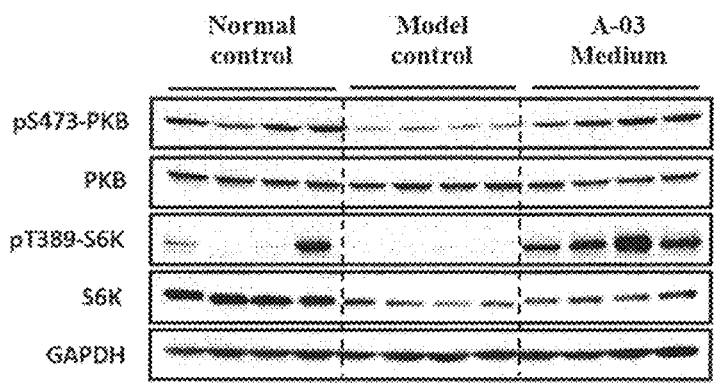
FIG. 22 shows the effect of A-03 drug on liver: (a) Western blotting showed the representative protein bands of pS473 PKB, PKB, pT389-S6k and S6K; (b) and (c) were the results of corresponding statistical analysis of expression, where 1-3 were the normal control group, the model control group and the A-03 medium dose administration group.
Figure 22:
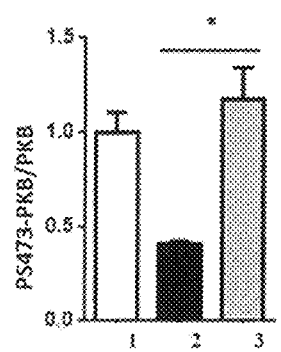
Figure 22:
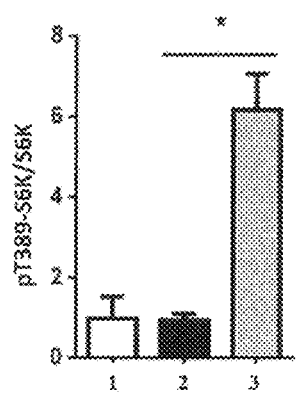

Tissue processing, protein electrophoretic separation and Western blotting are well known methods and will not be described here. FIG. 22 shows the effect of A-03 drug with an exemplary medium dose on the phosphorylation of key regulatory proteins of insulin sensitivity, including protein kinase B (PKB) and phosphorylated ribosomal protein S6 kinase (S6K). FIG. 22a shows the representative protein bands of pS473-PKB, PKB, pT389-S6K and S6K, while FIGS. 22b and 22c are the results of corresponding statistical analysis of expression (among them, 1-3 represents the normal control group, the model control group and the A-03 medium dose group sequentially). It can be seen that high-fat diet significantly reduced the proportion of phosphorylated protein kinase B in total protein (pS473-PKB/PKB). Compared with the model control group, A-03 drug administration significantly increased the phosphorylation of PKB protein ($P<0.05$, *), and significantly increased the protein ratio of phosphorylated ribosomal protein S6 kinase/ribosomal protein S6 kinase (pT389-S6K/S6K) ($P<0.05$, *). The results showed that A-03 drug significantly activated PKB-S6K signaling pathway, which increased the sensitivity of target cells to insulin and improved insulin resistance.

Figure 23:
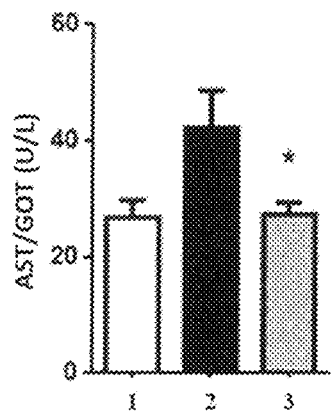
FIG. 23 shows the effect of A-03 administration on (a) glutamic oxaloacetic transaminase and (b) alanine aminotransferase in high-fat diet model mice, where 1-3 were the normal control group, the model control group and the A-03 medium dose administration group.
Figure 23:
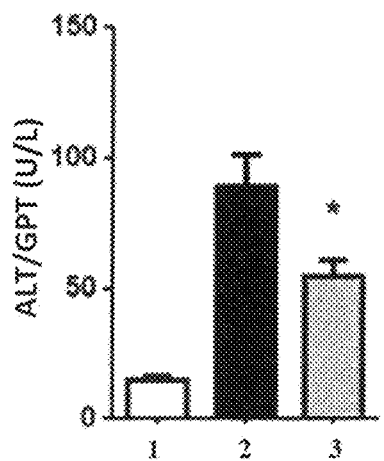

4.4.5.3 Protective effect on liver function injury caused by obese diabetes mellitus The detection methods of glutamic oxaloacetic transaminase and alanine aminotransferase in blood are well known and will not be repeated here. The detection of contents of glutamic oxaloacetic transaminase (AST) and alanine aminotransferase (ALT) in the blood of mice indicated that both AST and ALT were significantly increased in high-fat diet model mice. After A-03 drug treatment, very effective control was achieved. FIG. 23a and FIG. 23b show the effects of medium dose A-03 drug on AST or GOT and ALT or GPT respectively, where 1-3 in the histogram represents the normal control group, the model control group, and the A-03 medium dose administration group respectively. It can be seen that after A-03 drug administration, AST and ALT decreased significantly ($P<0.05$, *). This indicates that A-03 drug has a significant therapeutic effect on liver function damage caused by obese diabetes mellitus.

Other ligand-modified AuCs with different sizes also have similar effects. They would not be described in detail here.

INDUSTRIAL APPLICABILITY

AuCs can be used for the treatment of diabetes. They are suitable for industrial applications.

The invention claimed is:

1. A method for producing ligand-modified gold clusters (AuCs), said method comprising:
providing an $HAuCl_4$ solution;
sequentially adding an acidic solution and a first ligand solution into the $HAuCl_4$ solution to form a first mixture solution; wherein the molar ratio between the first ligand and $HAuCl_4$ is in the range of 1:1 to 20:1;
adding $NaBH_4$ solution into the first mixture solution to form a second mixture solution; wherein the molar ratio between $NaBH_4$ and $HAuCl_4$ is in the range of 1:1 to 10:1;
adding an aprotic polar solvent to the second mixture solution to terminate reaction and to obtain a third mixture solution;
centrifuging the third mixture solution to collect solid sediment;
dissolving the collected solid sediment in a second ligand solution to obtain a fourth mixture solution and maintaining the fourth mixture solution for a period; wherein the molar ratio between the second ligand and $HAuCl_4$ is in the range of 1:1 to 20:1;
centrifuging the fourth mixture solution to obtain supernatant; and
dialyzing the supernatant in a dialysis bag with a predetermined cut-off molecular size.

2. The method of claim 1, wherein the $HAuCl_4$ solution is composed of a neutral or acidic solvent selected from the group consisting of water, methanol, ethanol, n-propanol, 1-propanol, 2-propanol, 1-butanol, 2-butanol, pentanol, pentane, formic acid, acetic acid, diethyl ether, acetone, anisole, ethyl formate, methyl acetate, ethyl acetate, propyl acetate, isopropyl acetate, butyl acetate, isobutyl acetate, tributyl methyl ether, dimethyl sulfoxide, 2-methyl-1-propanol, and a mixture of two or more thereof.

3. The method of claim 1, wherein the acidic solution is composed of an acid selected from the group consisting of hydrochloric acid, phosphoric acid, sulfuric acid, acetic acid, propionic acid, butyric acid, and a mixture of two or more thereof.

4. The method of claim 1, wherein the first ligand and second ligand are selected from L-cysteine, D-cysteine and other cysteine derivatives; cysteine-containing oligopeptides and their derivatives; other thiol-containing compounds; and a mixture of two or more thereof.

5. The method of claim 1, wherein the first ligand solution and second ligand solution are composed of a solvent selected from the group consisting of water, methanol, ethanol, n-propanol, 1-propanol, 2-propanol, 1-butanol, 2-butanol, pentanol, ethyl formate, methyl acetate, ethyl acetate, propyl acetate, isopropyl acetate, butyl acetate, isobutyl acetate, 2-methyl-1-propanol, and a mixture of two or more thereof.

6. The method of claim 1, wherein the $NaBH_4$ solution is composed of a solvent selected from the group consisting of water, methanol, ethanol, n-propanol, 1-propanol, 2-propanol, 1-butanol, 2-butanol, pentanol, ethyl formate, methyl acetate, ethyl acetate, propyl acetate, isopropyl acetate, butyl acetate, isobutyl acetate, 2-methyl-1-propanol, and a mixture of two or more thereof.

7. The method of claim 1, wherein the aprotic polar solvent is selected from the group consisting of dimethyl sulfoxide (DMSO), acetone, acetonitrile, dimethylformamide (DMF), dimetbylacetamide (DMAC), hexamethylphosphoramide (HMP), chloroform, carbon tetrachloride, pyridine, and a mixture of two or more thereof.

8. The method of claim 1, wherein the period for maintaining the fourth mixture solution is in the range of 3-24 hours.

9. The method of claim 1, further comprising lyophilizing the dialyzed supernatant to obtain an AuCs powder.

10. An AuCs powder produced by claim 1.

11. A method for treating diabetes in a subject, wherein the method comprises:
administering a composition to the subject with diabetes: wherein the composition comprises a gold clusters (AuC); wherein said AuC comprises:
a gold core; and
a ligand modifying the gold core.

12. The use of claim 11, wherein the gold core has a diameter smaller than 3 nm.

13. The use of claim 11, wherein the gold core has a diameter in the range of 0.5-2.6 nm.

14. The use of claim 11, wherein the ligand is one selected from the group consisting of L-cysteine and its derivatives, D-cysteine and its derivatives, cysteine-containing oligopeptides and their derivatives, and other thiol-containing compounds.

15. The use of claim 14, wherein the L-cysteine and its derivatives are selected from the group consisting of L-cysteine, N-isobutyryl-L-cysteine (L-NIBC), and N-acetyl-L-cysteine (L-NAC), and wherein the D-cysteine and its derivatives are selected from the group consisting of D-cysteine, N-isobutyryl-D-cysteine (D-NIBC), and N-acetyl-D-cysteine (D-NAC).

16. The use of claim 14, wherein the cysteine-containing oligopeptides and their derivatives are cysteine-containing dipeptides, cysteine-containing tripeptides or cysteine-containing tetrapeptides.

17. The use of claim 16, wherein the cysteine-containing dipeptides are selected from the group consisting of L-cysteine-L-arginine dipeptide (CR), L-arginine-L-cysteine dipeptide (RC), L-histidine-L-cysteine dipeptide (HC), and L-cysteine-L-histidine dipeptide (CH).

18. The use of claim 16, wherein the cysteine-containing tripeptides are selected from the group consisting of glycine-L-cysteine-L-arginine tripeptide (GCR), L-proline-L-cysteine-L-arginine tripeptide (PCR), L-lysine-L-cysteine-L-proline tripeptide (KCP), and L-glutathione (GSH).

19. The use of claim 16, wherein the cysteine-containing tetrapeptides are selected from the group consisting of glycine-L-serine-L-cysteine-L-arginine tetrapeptide (GSCR), and glycine-L-cysteine-L-serine-L-arginine tetrapeptide (GCSR).

20. The use of claim 14, wherein the other thiol-containing compounds are selected from the group consisting of 1-[(2S)-2-methyl-3-thiol-1-oxopropyl]-L-proline, thioglycollic acid, mercaptoethanol, thiophenol, D-3-trolovol, N-(2-mercaptopropionyl)-glycine, and dodecyl mercaptan.

* * * * *